United States Patent
Benamou et al.

(10) Patent No.: US 11,426,507 B2
(45) Date of Patent: Aug. 30, 2022

(54) ARTHROSCOPIC DEVICES AND METHODS

(71) Applicant: RELIGN Corporation, Campbell, CA (US)

(72) Inventors: Steffan Benamou, Morgan Hill, CA (US); Michael D. Walker, San Francisco, CA (US); Aaron Germain, San Jose, CA (US)

(73) Assignee: Relign Corporation, Campbell, CA (US)

( * ) Notice: Subject to any disclaimer, the term of this patent is extended or adjusted under 35 U.S.C. 154(b) by 1046 days.

(21) Appl. No.: 16/105,447

(22) Filed: Aug. 20, 2018

(65) Prior Publication Data
US 2019/0134279 A1    May 9, 2019

Related U.S. Application Data

(60) Provisional application No. 62/548,297, filed on Aug. 21, 2017.

(51) Int. Cl.
*A61M 1/00* (2006.01)
*A61B 17/32* (2006.01)
(Continued)

(52) U.S. Cl.
CPC ............... *A61M 1/74* (2021.05); *A61B 1/015* (2013.01); *A61B 1/05* (2013.01); *A61B 1/317* (2013.01);
(Continued)

(58) Field of Classification Search
CPC ........ A61B 17/32002; A61B 2217/005; A61B 2218/007; A61B 18/1482; A61B 1/015;
(Continued)

(56) References Cited

U.S. PATENT DOCUMENTS 5,000,733 A * 3/1991 Mathies ................. A61B 1/12
                                                         604/118
5,125,801 A * 6/1992 Nabity ................. E21B 43/121
                                                         417/44.1
(Continued)

FOREIGN PATENT DOCUMENTS

CN       111565657 A     8/2020
EP         0529902 A2    3/1993
(Continued)

OTHER PUBLICATIONS

Allen-Bradley. AC Braking Basics. Rockwell Automation. Feb. 2001. 4 pages. URL: http://literature.rockwellautomation.com/idc/groups/literature/documents/wp/drives-wp004_-en-p.pdf.
(Continued)

*Primary Examiner* — Scott J Medway
(74) *Attorney, Agent, or Firm* — Schwegman Lundberg & Woessner, P.A.

(57) ABSTRACT

A fluid management system includes a pump connectable to a fluid source. An inflow line removably connects to a cannula for delivering a fluid flow from the pump into a surgical site, such as a joint cavity. A flow pressure sensor is coupled to measure flow pressure in the inflow line and produce a measured pressure value, A controller is connected to the pump and the flow pressure sensor, and the controller maintains a pressure set point by controlling a pump speed based on a backpressure-adjusted pressure value calculated by subtracting a backpressure value selected from a backpressure table from the measured pressure value. The BAPV is monitored to determine whether the BAPV deviates outside an initial BAPV range, and corrective measure are taken should such deviations occur.

17 Claims, 11 Drawing Sheets

(51) Int. Cl.

| | |
|---|---|
| *A61B 18/14* | (2006.01) |
| *A61B 90/98* | (2016.01) |
| *A61B 1/317* | (2006.01) |
| *A61B 1/015* | (2006.01) |
| *A61B 90/00* | (2016.01) |
| *A61B 1/05* | (2006.01) |
| *A61B 17/00* | (2006.01) |
| *A61B 18/12* | (2006.01) |
| *A61B 18/00* | (2006.01) |
| *A61M 5/168* | (2006.01) |

(52) U.S. Cl.
CPC ........ *A61B 17/32002* (2013.01); *A61B 18/14* (2013.01); *A61B 18/148* (2013.01); *A61B 18/149* (2013.01); *A61B 90/03* (2016.02); *A61B 90/98* (2016.02); *A61M 1/73* (2021.05); *A61M 1/77* (2021.05); *A61M 1/84* (2021.05); *A61B 18/1206* (2013.01); *A61B 2017/00022* (2013.01); *A61B 2017/00039* (2013.01); *A61B 2017/0088* (2013.01); *A61B 2017/00115* (2013.01); *A61B 2017/00119* (2013.01); *A61B 2017/00398* (2013.01); *A61B 2017/00464* (2013.01); *A61B 2018/00577* (2013.01); *A61B 2018/00589* (2013.01); *A61B 2018/00601* (2013.01); *A61B 2018/00744* (2013.01); *A61B 2018/00791* (2013.01); *A61B 2090/032* (2016.02); *A61B 2090/064* (2016.02); *A61B 2090/067* (2016.02); *A61B 2217/005* (2013.01); *A61B 2217/007* (2013.01); *A61B 2218/007* (2013.01); *A61M 1/00* (2013.01); *A61M 5/168* (2013.01); *A61M 2205/3334* (2013.01); *A61M 2205/3344* (2013.01)

(58) Field of Classification Search
CPC ............ A61M 2205/12; A61M 3/0258; A61M 1/0058; A61M 3/0216; A61M 3/022; A61M 1/73; A61M 2205/3331; A61M 2205/3344
See application file for complete search history.

(56) References Cited

U.S. PATENT DOCUMENTS

| | | | | | |
|---|---|---|---|---|---|
| 5,630,798 | A | * | 5/1997 | Beiser | A61B 1/00135 604/66 |
| 6,090,078 | A | * | 7/2000 | Erskine | A61M 25/0631 128/919 |
| 9,855,675 | B1 | | 1/2018 | Germain et al. | |
| 9,907,901 | B2 | | 3/2018 | Orczy-Timko et al. | |
| 10,022,140 | B2 | | 7/2018 | Germain et al. | |
| 10,052,149 | B2 | | 8/2018 | Germain et al. | |
| 10,076,593 | B2 | * | 9/2018 | Woolford | A61B 1/015 |
| 10,582,966 | B2 | | 3/2020 | Orczy-Timko et al. | |
| 10,595,889 | B2 | | 3/2020 | Germain et al. | |
| 2002/0062062 | A1 | * | 5/2002 | Belson | A61B 1/0053 600/146 |
| 2005/0015073 | A1 | * | 1/2005 | Kataishi | A61M 25/008 604/528 |
| 2005/0222535 | A1 | * | 10/2005 | Uesugi | A61B 1/042 604/26 |
| 2006/0286063 | A1 | * | 12/2006 | Shebuski | A61L 27/54 424/78.3 |
| 2007/0021713 | A1 | * | 1/2007 | Kumar | A61M 3/0258 604/27 |
| 2007/0078370 | A1 | | 4/2007 | Shener et al. | |
| 2007/0249993 | A1 | * | 10/2007 | Mollstam | A61B 1/126 604/65 |
| 2008/0091071 | A1 | * | 4/2008 | Kumar | A61M 1/0058 600/121 |
| 2008/0154095 | A1 | * | 6/2008 | Stubkjaer | A61M 3/0258 600/156 |
| 2010/0076372 | A1 | | 3/2010 | Hacker et al. | |
| 2010/0222632 | A1 | * | 9/2010 | Poirier | A61M 60/50 600/16 |
| 2013/0267779 | A1 | | 10/2013 | Woolford et al. | |
| 2013/0267894 | A1 | | 10/2013 | Woolford et al. | |
| 2013/0274549 | A1 | * | 10/2013 | Natale | A61B 1/015 600/104 |
| 2015/0174314 | A1 | * | 6/2015 | Shener | A61M 3/0216 604/151 |
| 2015/0250958 | A1 | * | 9/2015 | Hayashi | A61M 39/22 604/26 |
| 2016/0038007 | A1 | * | 2/2016 | Binmoeller | A61B 1/01 600/154 |
| 2016/0174814 | A1 | * | 6/2016 | Igov | A61B 17/0218 600/106 |
| 2016/0287779 | A1 | | 10/2016 | Orczy-timko et al. | |
| 2017/0258519 | A1 | | 9/2017 | Germain et al. | |
| 2019/0143010 | A1 | * | 5/2019 | Gaspredes | A61M 3/0216 604/35 |
| 2019/0261846 | A1 | * | 8/2019 | Oh | A61B 1/0002 |
| 2022/0001092 | A1 | | 1/2022 | Benamou et al. | |

FOREIGN PATENT DOCUMENTS

| | | |
|---|---|---|
| EP | 1909864 A2 | 4/2008 |
| EP | 3672505 A1 | 7/2020 |
| JP | 2020531155 A | 11/2020 |
| WO | WO-2017095679 A1 | 6/2017 |
| WO | WO-2019040381 A1 | 2/2019 |

OTHER PUBLICATIONS

Allen-Bradley. What Is Regeneration? Braking / Regeneration Manual: Regeneration Overview. Revision 1.0. Rockwell Automation. Accessed Apr. 24, 2017. 6 pages. URL: https://www.ab.com/support/abdrives/documentation/techpapers/RegenOverview01.pdf.

International search report with written opinion dated Dec. 13, 2018 for PCT/US18/47117.

"U.S. Appl. No. 17/482,090, Preliminary Amendment filed Sep. 29, 2021", 6 pgs.

"Chinese Application Serial No. 201880068616.9, Notification to Make Rectification dated May 8, 2020", W/English Translation, 2 pgs.

"European Application Serial No. 18848396.0, Extended European Search Report dated Jan. 18, 2021", 9 pgs.

"European Application Serial No. 18848396.0, Response filed Aug. 12, 2021 to Extended European Search Report dated Jan. 18, 2021", 23 pgs.

"International Application Serial No. PCT/US2018/047117, International Preliminary Report on Patentability dated Mar. 5, 2020", 11 pgs.

U.S. Appl. No. 17/482,090, filed Sep. 22, 2021, Arthroscopic Devices and Methods.

* cited by examiner

ARTHROSCOPIC DEVICES AND METHODS

CROSS-REFERENCE TO RELATED APPLICATION

This application claims the benefit of provisional application 62/548,297 filed on Aug. 21, 2017, the full disclosure of which is incorporated herein by reference.

BACKGROUND OF THE INVENTION

Field of the Invention

The present invention relates generally to medical devices and methods. More particularly, the invention relates to a medical system that integrates a fluid management system having controllable pumps, and a controller which controls the pumps to maintain a pressure set point in a surgical site.

In endoscopic and other surgical procedures including subacromial decompression, anterior cruciate ligament reconstruction involving notchplasty, and arthroscopic resection of the acromioclavicular joint, there is a need for cutting and removal of bone and soft tissue. Currently, surgeons use arthroscopic shavers and burrs having rotational cutting surfaces to remove hard tissue in such procedures.

In order to remove tissue chips and debris from a surgical site, many arthroscopic systems use a fluid management system (FMS) which pumps fluid through a cannula which used for positioning the arthroscopic device in the joint or other body cavity. The FMS usually also applies a suction to aspirate the surgical site through a passageway in the arthroscopic device. In a typical system, the FMS provides both pressure monitoring and control of the fluid being introduced to and aspirated from the body cavity. Such fluid management systems are illustrated, for example, in commonly owned U.S. Patent Publication No. 2017/0252099, the full disclosure of which is incorporated herein by reference.

Of particular pertinence to the present invention, such an FMS operates best with accurate measurement of the pressure in the joint or other body cavity. Often, however, pressure sensors are incorporated into an inlet line which delivers saline or other fluids to the joint cavity. As such remote pressure sensors measure a pressure that differs from the actual cavity pressure by a "backpressure" value that fluctuates based on the fluid flow rate. In particular, the measure values will be higher than the actual cavity pressures because of the pressure drop though the cannula and connecting tubing between the sensor and the body cavity. The pressure drop through the cannula will be increased by the presence of the arthroscope or other endoscope in the cannula lumen which delivers the fluid.

To address this problem, some FMS utilize a "backpressure table" that is generated prior to each procedure by running the pump to deliver fluid through the cannula into free space to determine the backpressure between the pressure sensor and the outlet end of the cannula as a function of flow rate. More specifically, the backpressure values are measured with the arthroscope or other endoscope placed within the cannula lumen so that the fluid pathway replicates that which the FMS will see during the procedure. Backpressure values can be determined from the backpressure table based upon flow rate, and those backpressure values can be subtracted from the value measure by the remote pressure sensor to provide a more accurate pressure reading.

This approach works well so long as the fluid pathway through the cannula and connecting tubing remains as it was during the initial generation of the backpressure table. Often, however, the pathway will change materially, For example, at different points during the procedure, the cannula may be exchanged, and the change will significantly affect the backpressure. Such a change can be problematic, particularly if the actual backpressures are lower than those in the backpressure table, i.e., the table backpressures are higher than the actual backpressures and the "adjusted" cavity pressures are lower than the actual cavity pressures. Adjusted body cavity pressures which are too low will cause the FMS to increase the pump speed to raise the cavity pressure above the nominal set point which can be a risk to the patient.

It is therefore an object of the present invention to provide improved fluid management systems for performing arthroscopic and other endoscopic procedures. In particular, it would be desirable to provide a FMS which can correct cavity pressure measurements by subtracting backpressures from pressure sensor readings with a reduced risk of inaccuracy should actual backpressures change during a procedure. It is a specific object of this invention to provide a FMS which can determine when an assumed backpressure falls outside of an expected range and to further provide alternate pressure correction protocols when such deviations occur. At least some of these objectives will be met by the inventions described herein.

Description of the Background Art

U.S. Patent Publication No. 2017/0252099 has been described above.

SUMMARY OF THE INVENTION

The present invention provides improved fluid management systems (FMS) of a type which can be used with arthroscopic, laparoscopic, and other endoscopic surgical tools and apparatus for preforming minimally invasive surgically procedures, particularly arthroscopic producers on a joint, such as a knee, shoulder, hip, or other joint. Such FMS according to the present invention are configured to control pressure of a fluid being pumped into the joint or other surgical worksite by a controllable pump which is part of the FMS. Real time pressure is measured by a pressure sensor in a fluid line between the controllable pump and the worksite, usually located in a fluid inlet line which is removably connectable to a cannula or sheath being used to access the worksite. In some instances, the pressure sensor may be in a tube which is part of a cassette for a peristaltic pump as described elsewhere herein. The pressure measured by the pressure sensor is adjusted by the FMS to account for a backpressure present in the fluid inlet line and in all other components in the flow path between the pump and the worksite, usually including at least a lumen in a cannula through which the fluid is delivered. For example, such adjustment may be achieved using a backpressure table which may be generated for each procedure, typically immediately prior to the procedure after the cannula and endoscope have been assembled, by measuring the backpressure sensed by the pressure sensor at different fluid flow rates delivered by the pump. In particular, the pump is controlled to deliver fluid through the inlet line, cannula, and any other tubes or components in the fluid delivery path, and the fluid is delivered into a free space, e.g., an open container or other receptacle. The measured pressures are thus representative of the backpressure in the fluid delivery path at each flow rate so that the table can be generated for subsequent look up during use of the FMS to control the pump and maintain a target pressure. The backpressure table generated at the beginning of each protocol is referred to as the "initial" backpressure table and is used to calculate a backpressure-adjusted pressure value (BAPV) by subtracting the backpressure value for that flow rate from a value measured by the pressure sensor at any given flow rate. The initial backpressure table can be used for so long as there are no significant changes in the flow path between the pump and the outlet end of the cannula which is delivering the fluid to the body cavity. If there are any significant changes come up, for example, the cannula is changed, then the initial backpressure table will be most likely be unable to provide accurate pressure adjustment.

Such use of backpressure adjustment tables is known, and the present invention further provides for remediating steps when the initial backpressure table can no longer be relied upon, typically because the configuration of the inlet line, cannula, endoscope, or other component of the fluid delivery flow path has changed. In particular, the present invention can provide an "alternative" backpressure table that can be relied on should the initial backpressure table become unreliable. In a specific embodiment, the alternative backpressure table will include backpressure values which are representative of the backpressure provided by the fluid inlet line of the FMS only. As the fluid inlet line will not significantly change configuration during normal use of the FMS, the actual backpressure in FMS connected to a cannula will never be less in that of the fluid inlet line alone. Thus, by using the alternative backpressure table, the pressure value determined for the cavity pressure will never be less than the actual pressure so that FMS will be less likely to deliver excess fluid and over pressurizing the cavity based on an apparent cavity pressure which is lower than the actual cavity pressure.

In a first aspect, the present invent provides a system for treating tissue. A fluid management system includes a pump which can be connected to fluid a source, such as saline. An inflow line is configured to be removably connected to a cannula for delivering a fluid flow from the pump into a working space, such as a joint cavity or a like. A flow pressure sensor is located to measure flow pressure in the inflow line to generate a measured pressure signal or value. In specific examples, the flow pressure sensor may be located in or near a pump cassette as described in various embodiments below. The FMS further includes a controller which is connected to the pump and to the flow pressure sensor. The controller is configured to maintain a pressure set point by controlling a pump speed based on an initial backpressure-adjusted pressure value (BAPV) calculated by subtracting a backpressure value selected from an initial backpressure table from the measured pressure value to produce an adjusted pressure value. The controller further monitors the initial BAPV to determine if the initial BAPV remains within an expected initial BAPV range The initial BAPV range will vary depending on the pump speed and/or fluid flow rate. That is, for any initial BAPV calculated any given flow rate and/or pump speed, value should never fall below 0. The value will fall below 0 if, for example, a cannula is replaced with another cannula having a much lower flow resistance, e.g., a cannula or sheath which fits much more loosely over a particular arthroscope. The actual backpressure will be much lower than the initial backpressure derived from the initial backpressure table at any given flow rate. Thus, when the BAPV is calculated by the FMS, the backpressure from the table will be higher than the actual backpressure, and subtraction from the measured pressure and the cavity will typically fall below 0. This will result in a higher inlet flow than is needed and raised the pressure within the cavity to potentially deleterious levels.

In a specific embodiment of the methods of present invention, the initial backpressure table will be populated with backpressure values measured while operating the FMS at different pump speeds when the pump is connected to the inflow line, the cannula, and any other components of the inflow system, while the distal end of the cannula is in free space. Usually, the initial backpressure table will be generated at the beginning of each procedure with the arthroscope or endoscope inserted within the cannula lumen so that the backpressure table most accurately represents the actual backpressures that will be encountered during the procedure. After the initial backpressure table is generated, the assembly of the cannula and arthroscope may then be introduced to the joint cavity or other surgical site, and the procedure commenced.

In further specific embodiments of the methods herein, the controller will be further configured to continue to maintain the pressure set point by controlling the pump speed based on initial BAPV for so long as the initial BAPV remains within the expected initial BAPV range. Should the initial BAPV fall outside of the expected initial BAPV range, however, the controller is further configured to access the alternative backpressure table which represents backpressure values between the flow pressure sensor and end of the inflow line of the FMS in free space at different flows generated by the pump. Typically, the alternative backpressure table may be generated for the FMS for use in multiple procedures and need not generated for each procedure or protocol prior to commencement. The arrangement of the pump, flow pressure sensor, inlet flow line, end line, will generally remain unchanged as successive procedures are performed with the FMS, so a system-specific alternative backpressure table can be generated for the FMS and stored for future use in the controller. This is in contrast to the assembly of the cannula, arthroscope, and/or other components which are attached to the inflow line which would generally be changed for each protocol and often be further changed during the protocol.

In further specific embodiments of the methods herein, the controller of the FMS maybe configured to re-access the initial backpressure table if and when the initial BAPV returns to a value within the initial BAPV range. It will be appreciated that operating with the initial backpressure table is preferred since the pressure within the joint cavity or other surgical worksite is maintained at a value closer to the desired pressure set point. Thus, when the system recognizes that the initial BAPV has returned to a value within the initial BAPV range, and is thus again reliable; the FMS may revert to control based on the initial BAPV table.

In yet another specific embodiment of the methods herein, the controller may be further configured to access a "replacement" backpressure table which is typically generated during the procedure after the initial BAPV has fallen outside of the BAPV range. In contrast to using the alternative backpressure table, which is typically stored within the controller, the replacement backpressure table will be generated during the procedure by measuring backpressures at multiple flows rates produce by the pump when connected to the inflow line and a replacement cannula and/or other reconfigured flow deliver components, to then produce an accurate backpressure table for the system as configured at that time during the procedure. The replacement backpressure table thus represents a "reboot" of the FMS after the inflow resistance has changed, for example by exchanging the cannula being used.

Other aspects of the system are typical of fluid management systems of the type described herein and other related patents and applications commonly owned here with. For example, the pump may comprise an inflow unit connected to the inflow line and the outflow unit connected to the outflow line. The endoscope may be configured for minimally invasive insertion into the working space, and further configured for removable attachment to the inflow line and having a lumen for a delivery of fluid from the fluid source. The systems may further comprise and interventional tool configured for insertion through the lumen of the endoscope and may further have an extraction channel for connection to outflow line.

In a second aspect, the present invention provides methods for treating tissue. The methods comprise pumping fluid through an inlet line connected to a cannula having a distal or outflow end in a surgical site using a pump. A pressure value is measured using a pressure sensor in the inlet line, and an initial backpressure-adjusted pressure value (BAPV) is calculated by subtracting a backpressure value selected from an initial backpressure table from the measured value. A pump speed of the pump is controlled to maintain the initial BAPV at a pressure set point, and initial BAPV is monitored to determine if the initial BAPV remains within an expected initial BAPV range. The pump speed will be controlled to maintain the initial BAPV at the pressure set point for so long as the initial BAPV remains within the expected initial BAPV range.

In specific embodiments of the methods herein, an alternative backpressure table will be accessed when the initial BAPV falls outside of the expected initial BAPV range. The alternative backpressure table includes backpressure values measured between the flow pressure sensor and end of the inflow line in free space at different flow rates generated by the pump. Thus, the alternative backpressure table differs from the initial backpressure table the backpressure values will be lower since they are determined based on the presents of the inflow line only, and any contribution to backpressure by the cannula, endoscope and the cannula lumen, or other downstream components is removed. In this way, the alternative backpressure table represents a "fail safe" option since the backpressure values are lower and subtracting those values from the measured pressure values will give an apparent higher pressure which will cause the FMS to deliver less fluid to meet the pressure set point.

In still furthers specific embodiments of the methods herein, even after the system begins operating using the alternative backpressure table, the FMS will continue to monitor the initial BAPV, by continuing to calculate initial BAPV values by subtracting initial backpressure values from the measured pressure values to determine if the initial BAPV has returned to a value within the expected initial backpressure range.

In a still further specific embodiment to the methods herein, a replacement backpressure table may be generated by measuring backpressure values at multiple flow rates using a replacement cannula after the initial BAPV has fallen outside of the initial BAPV range. In such instances, a replacement BAPV may be calculated by adding a backpressure value selected from the backpressure table to the measured pressure value. The pump speed may then be controlled based on the replacement BAPV and the pressure set point. It would be appreciated that generated the backpressure table represents "reboot" of the system and will be typically performed by the operating team during the procedure after significant reconfiguration of the cannula and/or other components of the fluid downstream from the inflow line.

BRIEF DESCRIPTION OF THE DRAWINGS

Various embodiments of the present invention will now be discussed with reference to the appended drawings. It should be appreciated that the drawings depict only typical embodiments of the invention and are therefore not to be considered limiting in scope.

DETAILED DESCRIPTION OF THE INVENTION

The present invention relates to bone cutting and tissue removal devices and related methods of use. Several variations of the invention will now be described to provide an overall understanding of the principles of the form, function and methods of use of the devices disclosed herein. In general, the present disclosure provides for variations of arthroscopic tools adapted for cutting bone, soft tissue, meniscal tissue, and for RF ablation and coagulation. The arthroscopic tools are typically disposable and are configured for detachable coupling to a non-disposable handpiece that carries a motor drive component. This description of the general principles of this invention is not meant to limit the inventive concepts in the appended claims.

Figure 1:
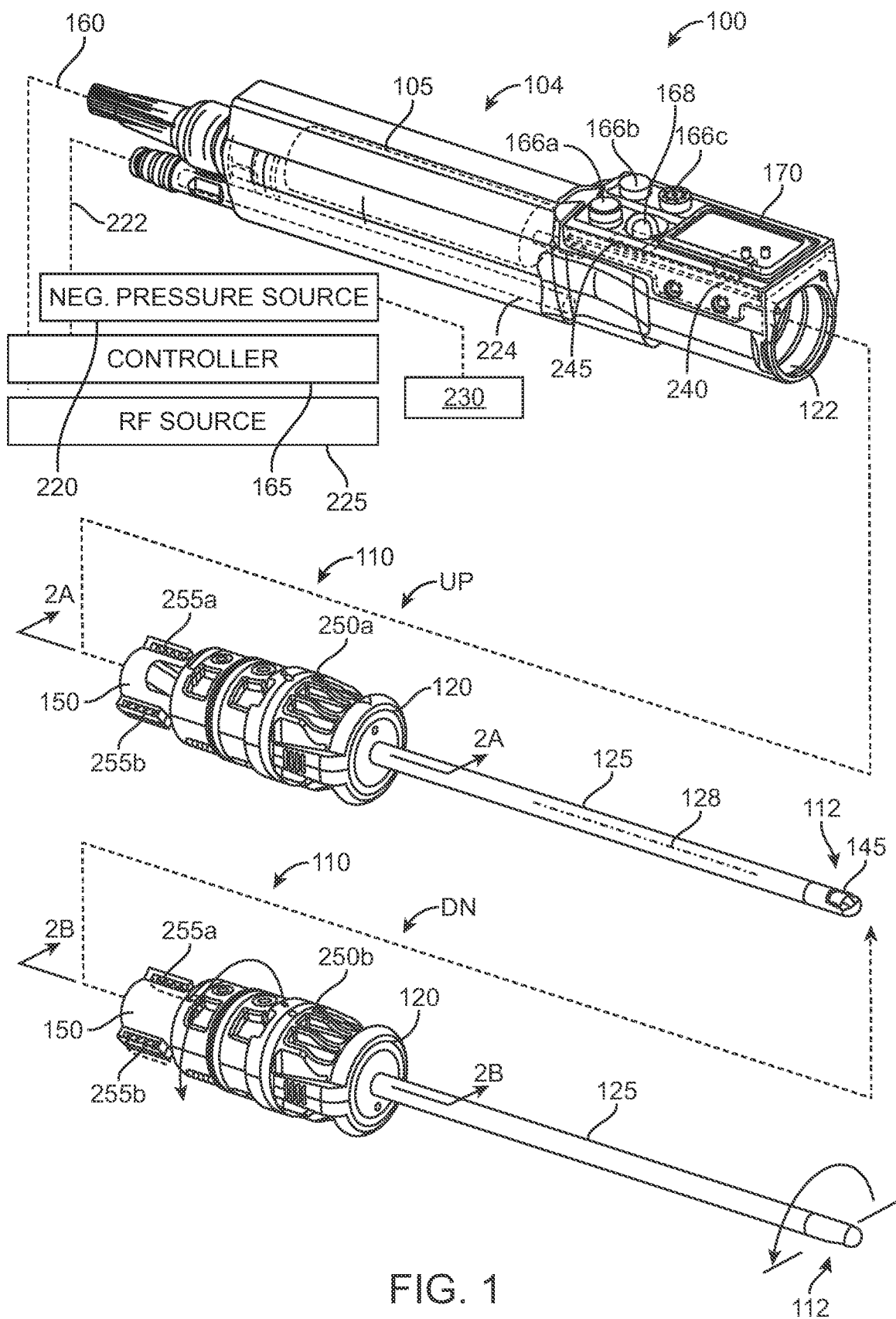
FIG. 1 is a perspective view of an arthroscopic cutting system that includes reusable handpiece with a motor drive and a detachable single-use cutting probe, wherein the cutting probe is shown in two orientations as it may be coupled to the handpiece with the probe and working end in upward orientation or a downward orientation relative to the handpiece, and wherein the handpiece includes an LCD screen for displaying operating parameters of system during use together with control actuators on the handpiece.

In one variation shown in FIG. 1, the arthroscopic system 100 of the present invention provides a handpiece 104 with motor drive 105 and a disposable shaver assembly or probe 110 with a proximal hub 120 that can be received by receiver or bore 122 in the handpiece 104. In one aspect, the probe 110 has a working end 112 that carries a high-speed rotating cutter that is configured for use in many arthroscopic surgical applications, including but not limited to treating bone in shoulders, knees, hips, wrists, ankles and the spine.

Figure 2A:
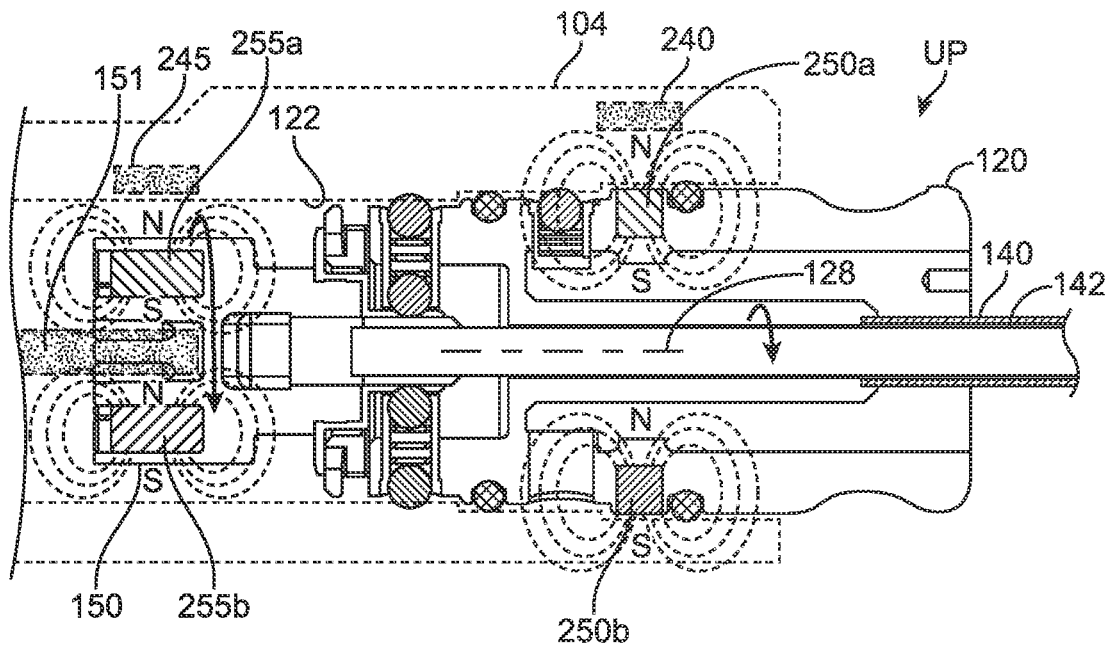
FIG. 2A is an enlarged longitudinal sectional view of the hub of the probe of FIG. 1 taken along line 2A-2A of FIG. 1 with the hub and probe in an upward orientation relative to the handpiece, further showing Hall effect sensors carried by the handpiece and a plurality of magnets carried by the probe hub for device identification, for probe orientation and determining the position of motor driven components of the probe relative to the handpiece.
Figure 3A:
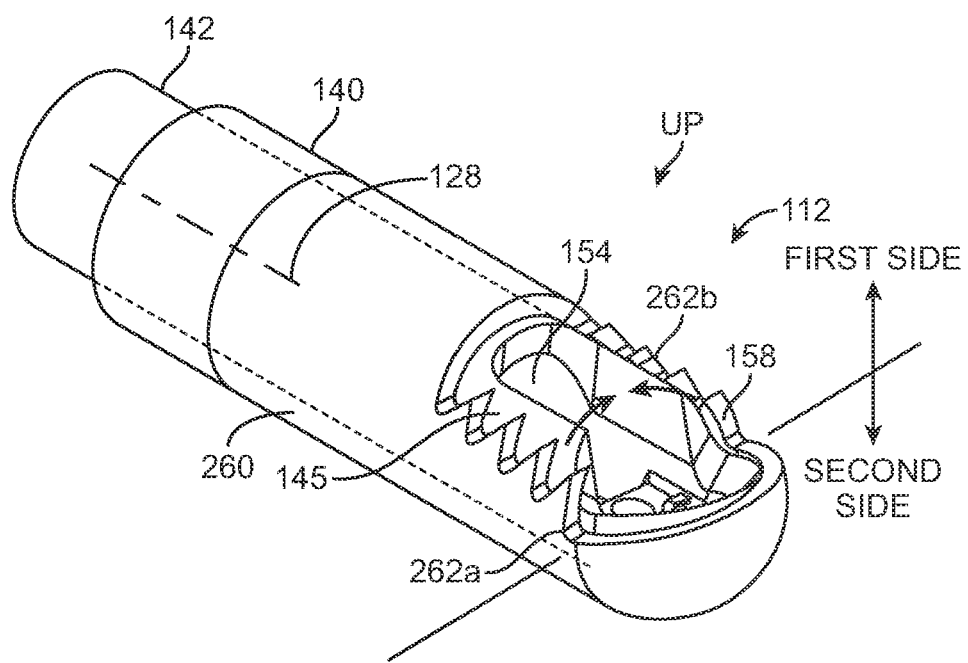
FIG. 3A is an enlarged perspective view of the working end of the probe of FIG. 1 in an upward orientation with the rotatable cutting member in a first position relative to the outer sleeve wherein the window in the cutting member is aligned with the window of the outer sleeve.
Figure 3B:
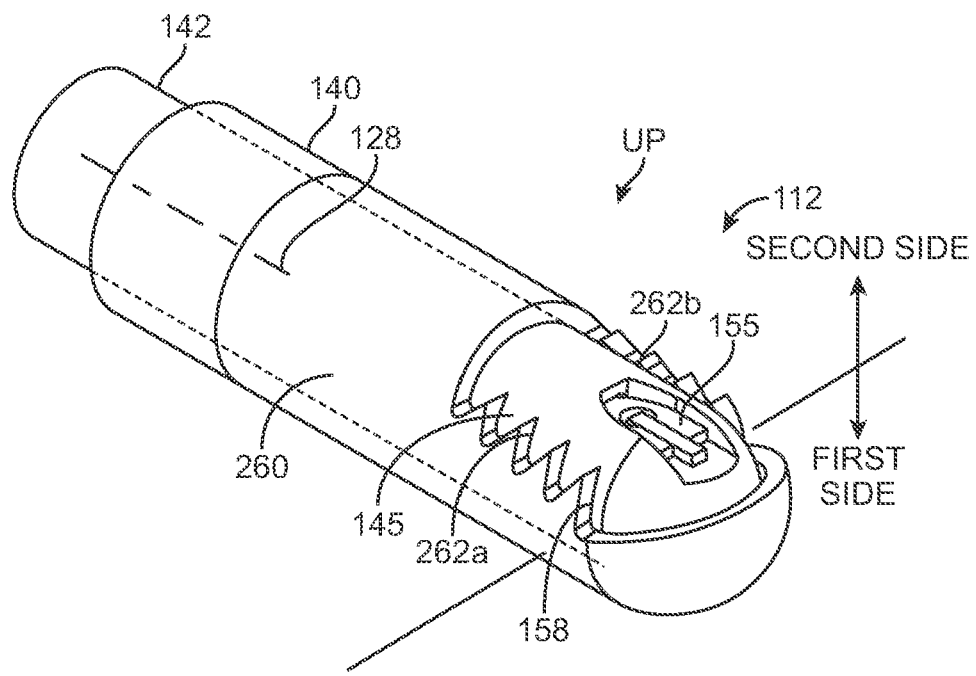
FIG. 3B is a perspective view of the working end of FIG. 1 in an upward orientation with the rotatable cutting member in a second position relative to the outer sleeve wherein the electrode carried by the cutting member is aligned with a centerline of the window of the outer sleeve.

In FIGS. 1, 2A and 3A, it can be seen that probe 110 has a shaft 125 extending along longitudinal axis 128 that comprises an outer sleeve 140 and an inner sleeve 142 rotatably disposed therein with the inner sleeve 142 carrying a distal ceramic cutting member 145 (FIG. 3A). The shaft 125 extends from the proximal hub 120 wherein the outer sleeve 140 is coupled in a fixed manner to the hub 120 which can be an injection molded plastic, for example, with the outer sleeve 140 insert molded therein. The inner sleeve 142 is coupled drive coupling 150 that is configured for coupling to the rotating motor shaft 151 of motor drive unit 105. More in particular, the rotatable cutting member 145 that is fabricated of a ceramic material with sharp cutting edges on opposing sides 152a and 152b of window 154 therein for cutting soft tissue. The motor drive 105 is operatively coupled to the ceramic cutter to rotate the cutting member at speeds ranging from 1,000 rpm to 20,000 rpm. In FIG. 3B, it can be seen that cutting member 145 also carries an RF electrode 155 in a surface opposing the window 154. The cutting member 145 rotates and shears tissue in the toothed opening or window 158 in the outer sleeve 140 (FIG. 3A). A probe of the type shown in FIG. 1 is described in more detail in co-pending and commonly owned patent application Ser. No. 15/421,264 filed Jan. 31, 2017 titled ARTHROSCOPIC DEVICES AND METHODS which is incorporated herein in its entirety by this reference.

As can be seen in FIG. 1, the probe 110 is shown in two orientations for detachable coupling to the handpiece 104. More particularly, the hub 120 can be coupled to the handpiece 104 in an upward orientation indicated at UP and a downward orientation indicated at DN where the orientations are 180° opposed from one another. It can be understood that the upward and downward orientations are necessary to orient the working end 112 either upward or downward relative to the handpiece 104 to allow the physician to interface the cutting member 145 with targeted tissue in all directions without having to manipulate the handpiece in 360° to access tissue.

In FIG. 1, it can be seen that the handle 104 is operatively coupled by electrical cable 160 to a controller 165 which controls the motor drive unit 105 Actuator buttons 166a, 166b or 166c on the handle 104 can be used to select operating modes, such as various rotational modes for the ceramic cutting member 145. In one variation, a joystick 168 can be moved forward and backward to adjust the rotational speed of the ceramic cutting member 145. The rotational speed of the cutter can continuously adjustable, or can be adjusted in increments up to 20,000 rpm. An LCD screen 170 is provided in the handpiece for displaying operating parameters, such as cutting member RPM, mode of operation, etc.

Figure 4:
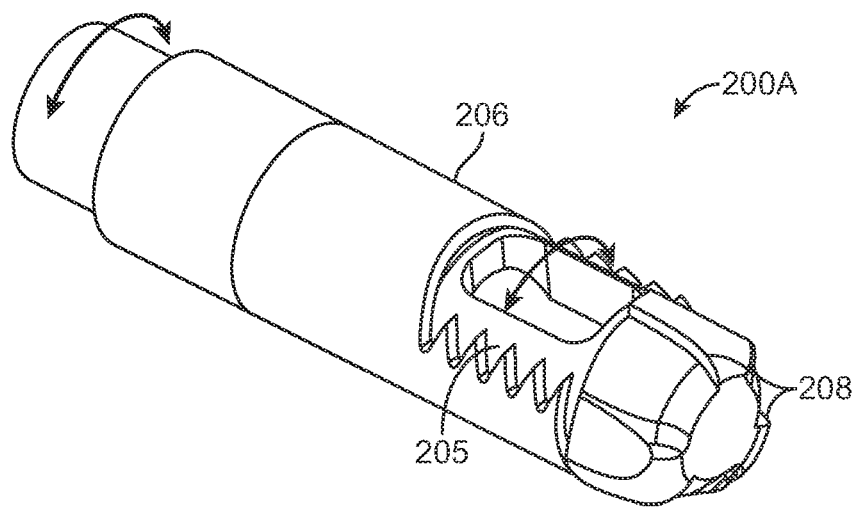
FIG. 4 is a perspective view of a working end of a variation of a probe that may be detachably coupled to the handpiece of FIG. 1, wherein the working end includes a bone burr extending distally from the outer sleeve.
Figure 5:
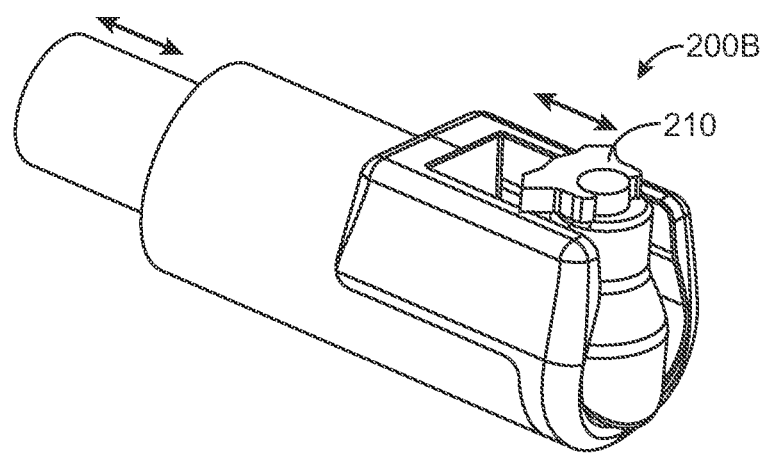
FIG. 5 is a perspective view of a working end of a variation of a probe that may be detachably coupled to the handpiece of FIG. 1, wherein the working end has a reciprocating electrode.
Figure 6:
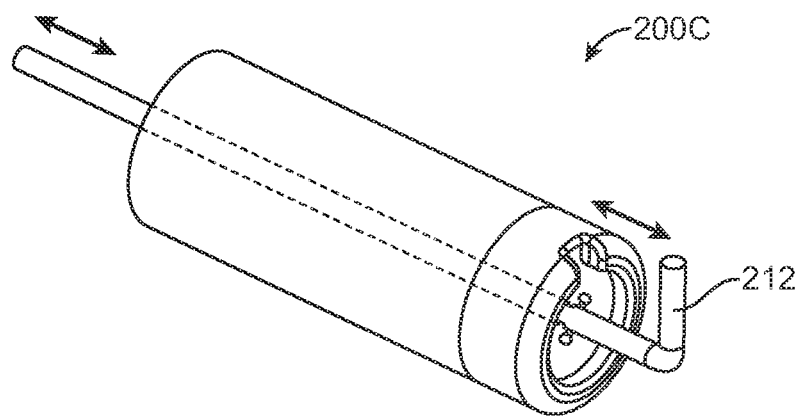
FIG. 6 is a perspective view of a working end of another variation of a probe that may be detachably coupled to the handpiece of FIG. 1, wherein the working end has a hook electrode that has extended and non-extended positions.
Figure 7:
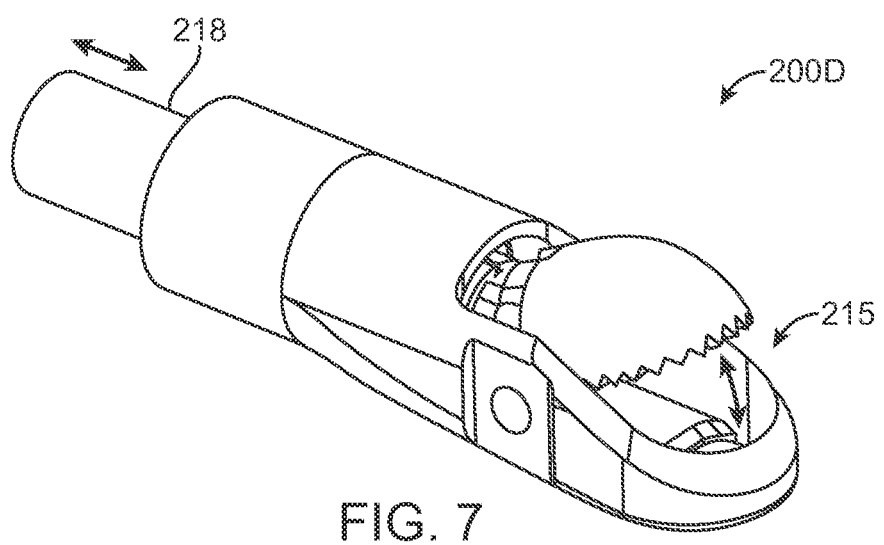
FIG. 7 is a perspective view of a working end of yet another variation of a probe that may be detachably coupled to the handpiece of FIG. 1, wherein the working end has an openable-closeable jaw structure for cutting tissue.

It can be understood from FIG. 1 that the system 100 and handpiece 104 is adapted for use with various disposable probes which can be designed for various different functions and procedures For example, FIG. 4 illustrates a different variation of a probe working end 200A that is similar to working end 112 of probe 110 of FIGS. 3A-3B, except the ceramic cutting member 205 extends distally from the outer sleeve 206 and the cutting member has burr edges 208 for cutting bone. The probe of FIG. 4 is described in more detail in co-pending and commonly owned patent application Ser. No. 15/271,184 filed Sep. 20, 2016 titled ARTHROSCOPIC DEVICES AND METHODS. FIG. 5 illustrates a different variation of a probe working end 200B with a reciprocating electrode 210 in a type of probe described in more detail in co-pending and commonly owned patent application Ser. No. 15/410,723 filed Jan. 19, 2017 titled ARTHROSCOPIC DEVICES AND METHODS. In another example, FIG. 6 illustrates another variation of a probe working end 200C that has an extendable-retractable hook electrode 212 in a probe type described in more detail in co-pending and commonly owned patent application Ser. No. 15/454,342 filed Mar. 9, 2017 titled ARTHROSCOPIC DEVICES AND METHODS. In yet another example, FIG. 7 illustrates a variation of a working end 200D in a probe type having an openable-closable jaw structure 215 actuated by reciprocating member 218 for trimming meniscal tissue or other tissue as described in more detail in co-pending and commonly owned patent application Ser. No. 15/483,940 filed Apr. 10, 2017 titled ARTHROSCOPIC DEVICES AND METHODS. All of the probes of FIGS. 4-7 can have a hub similar to hub 120 of probe 110 of FIG. 1 for coupling to the same handpiece 104 of FIG. 1, with some of the probes (see FIGS. 5-7) having a hub mechanism for converting rotational motion to linear motion. All of the patent applications just identified in this paragraph are incorporated herein by this reference.

FIG. 1 further shows that the system 100 also includes a negative pressure source 220 coupled to aspiration tubing 222 which communicates with a flow channel 224 in handpiece 104 and can cooperate with any of the probes 110, 200A, 200B or 200C of FIGS. 1-3B, 4, 5 and 6. In FIG. 1 it also can be seen that the system 100 includes an RF source 225 which can be connected to an electrode arrangement in any of the probes 110, 200A, 200B or 200C of FIGS. 1-3B, 4, 5 and 6. The controller 165 and microprocessor therein together with control algorithms are provided to operate and control all functionality, which includes controlling the motor drive 105 to move a motor-driven component of any probe working end 110, 200A, 200B or 200C, as well as for controlling the RF source 225 and the negative pressure source 220 which can aspirate fluid and tissue debris to collection reservoir 230.

As can be understood from the above description of the system 100 and handpiece 104, the controller 165 and controller algorithms need to be configured to perform and automate many tasks to provide for system functionality. In a first aspect, controller algorithms are needed for device identification so that when any of the different probes types 110, 200A, 200B, 200C or 200D of FIGS. 1 and 4-7 are coupled to handpiece 104, the controller 165 will recognize the probe type and then select algorithms for operating the motor drive 105, RF source 225 and negative pressure source 220 as is needed for the particular probe. In a second aspect, the controller is configured with algorithms that identify whether the probe is coupled to the handpiece 104 in an upward or downward orientation relative to the handpiece, wherein each orientation requires a different subset of the operating algorithms. In another aspect, the controller has separate control algorithms for each probe type wherein some probes have a rotatable cutter while others have a reciprocating electrode or jaw structure. In another aspect, most if not all the probes 110, 200A, 200B, 200C and 200D (FIGS. 1, 4-7) require a default "stop" position in which the motor-driven component is stopped in a particular orientation within the working end. For example, a rotatable cutter 145 with an electrode 155 needs to have the electrode centered within an outer sleeve window 158 in a default position such as depicted in FIG. 3B. Some of these systems, algorithms and methods of use are described next.

Figure 2B:
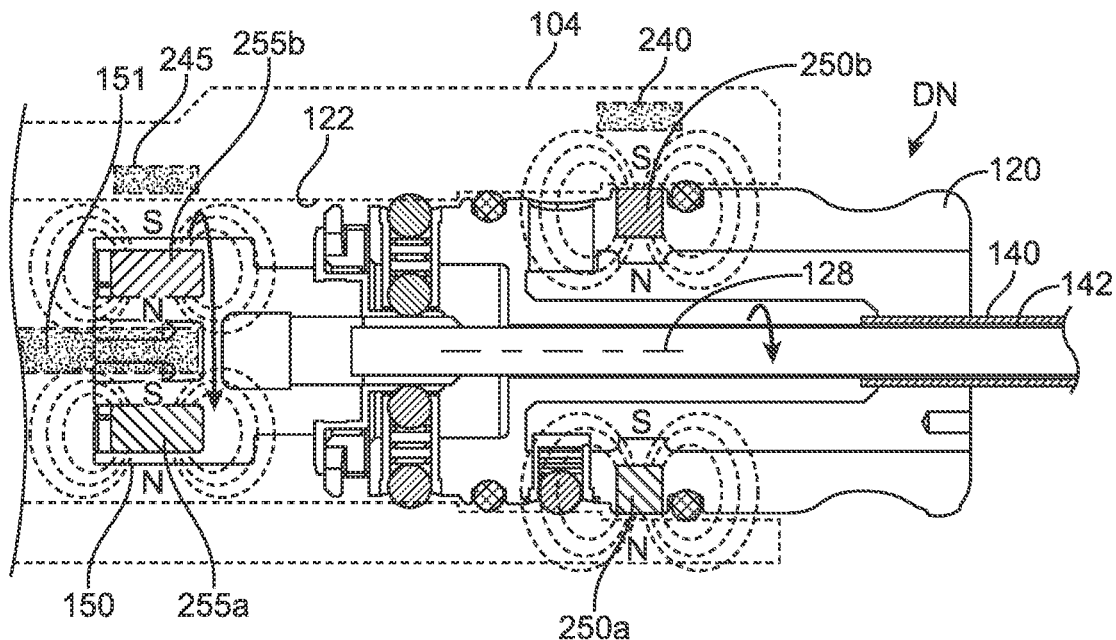
FIG. 2B is a sectional view of the hub of FIG. 1 taken along line 2B-2B of FIG. 1 with the hub and probe in a downward orientation relative to the handpiece showing the Hall effect sensor and magnets having a different orientation compared to that of FIG. 2A.

Referring to FIGS. 1 and 2A-2B, it can be seen that handpiece 104 carries a first Hall effect sensor 240 in a distal region of the handpiece 104 adjacent the receiving passageway 122 that receives the hub 120 of probe 110. FIG. 2A corresponds to the probe 110 and working end 112 in FIG. 1 being in the upward orientation indicated at UP. FIG. 2B corresponds to probe 110 and working end 112 in FIG. 1 being in the downward orientation indicated at DN. The handpiece 104 carries a second Hall effect sensor 245 adjacent the rotatable drive coupling 150 of the probe 110. The probe 110 carries a plurality of magnets as will be described below that interact with the Hall effect sensors 240, 245 to provide multiple control functions in cooperation with controller algorithms, including (i) identification of the type of probe coupled to the handpiece, (ii) the upward or downward orientation of the probe hub 120 relative to the handpiece 104, and (iii) the rotational position and speed of rotating drive collar 150 from which a position of either rotating or reciprocating motor-driven components can be determined.

The sectional views of FIGS. 2A-2B show that hub 120 of probe 110 carries first and second magnets 250a and 250b in a surface portion thereof. The Hall sensor 240 in handpiece 104 is in axial alignment with either magnet 250a or 250b when the probe hub 120 is coupled to handpiece 104 in an upward orientation (FIGS. 1 and 2A) or a downward orientation (FIGS. 1 and 2B). In one aspect as outlined above, the combination of the magnets 250a and 250b and the Hall sensor 240 can be used to identify the probe type. For example, a product portfolio may have from 2 to 10 or more types of probes, such as depicted in FIGS. 1 and 4-7, and each such probe type can carry magnets 250a, 250b having a specific, different magnetic field strength. Then, the Hall sensor 240 and controller algorithms can be adapted to read the magnetic field strength of the particular magnet(s) in the probe which can be compared to a library of field strengths that correspond to particular probe types. Then, a Hall identification signal can be generated or otherwise provided to the controller 165 to select the controller algorithms for operating the identified probe, which can include parameters for operating the motor drive 105, negative pressure source 220 and/or RF source 225 as may be required for the probe type. As can be seen in FIGS. 1, 2A and 2B, the probe hub 120 can be coupled to handpiece 104 in upward and downward orientations, in which the North (N) and South (S) poles of the magnets 250a, 250b are reversed relative to the probe axis 128. Therefore, the Hall sensor 240 and associated algorithms look for magnetic field strength regardless of polarity to identify the probe type.

Referring now to FIGS. 1, 2A-2B and 3A-3B, the first and second magnets 250a and 250b with their different orientations of North (N) and South (S) poles relative to central longitudinal axis 128 of hub 120 are also used to identify the upward orientation UP or the downward orientation DN of hub 120 and working end 112. In use, as described above, the physician may couple the probe 110 to the handpiece receiving passageway 122 with the working end 112 facing upward or downward based on his or her preference and the targeted tissue. It can be understood that controller algorithms adapted to stop rotation of the cutting member 145 in the window 158 of the outer sleeve 104 of working end 112 need to "learn" whether the working end is facing upward or downward, because the orientation or the rotating cutting member 145 relative to the handpiece and Hall sensor 240 would vary by 180°. The Hall sensor 240 together with a controller algorithm can determine the orientation UP or the downward orientation DN by sensing whether the North (N) or South (S) pole of either magnet 250a or 250b is facing upwardly and is proximate the Hall sensor 240.

In another aspect of the invention, in probe 110 (FIG. 1) and other probes, the motor-driven component of a working end, such as rotating cutter 145 of working end 112 of FIGS. 1 and 3A-3B needs to stopped in a selected rotational position relative to a cut-out opening or window 158 in the outer sleeve 140. Other probe types may have a reciprocating member or a jaw structure as described above, which also needs a controller algorithm to stop movement of a moving component in a selected position, such as the axial-moving electrodes of FIGS. 5-6 and the jaw structure of FIG. 7. In all probes, the motor drive 105 couples to the rotating drive coupling 150, thus sensing the rotational position of the drive coupling 150 can be used to determine the orientation of the motor-driven component in the working end. More in particular, referring to FIGS. 1 and 2A-2B, the drive coupling 150 carries third and fourth magnets 255a or 255b with the North (N) and South (S) poles of magnets 255a or 255b being reversed relative to the probe axis 128. Thus, Hall sensor 245 can sense when each magnet rotates passes the Hall sensor and thereby determine the exact rotational position of the drive coupling 150 twice on each rotation thereof (once for each magnet 255a, 255b). Thereafter, a controller tachometer algorithm using a clock can determine and optionally display the RPM of the drive coupling 150 and, for example, the cutting member 145 of FIG. 3A.

In another aspect of the invention, the Hall sensor 245 and magnets 255a and 255b (FIGS. 1 and 2A) are used in a set of controller algorithms to stop the rotation of a motor-driven component of a working end, for example, cutting member 145 of FIGS. 1 and 3A-3B in a pre-selected rotational position. In FIG. 3A, it can be seen that the inner sleeve 142 and a "first side" of cutting member 145 and window 154 therein is stopped and positioned in the center of window 158 of outer sleeve 140. The stationary position of cutting member 145 and window 154 in FIG. 3A may be used for irrigation or flushing of a working space to allow for maximum fluid outflow through the probe.

FIG. 3B depicts inner sleeve 142 and a "second side" of cutting member 145 positioned about the centerline of window 158 in the outer sleeve 140. The stationary or stopped position of cutting member 145 in FIG. 3B is needed for using the RF electrode 155 to ablate or coagulate tissue. It is important that the electrode 155 is maintained along the centerline of the outer sleeve window 158 since the outer sleeve 140 typically comprises return electrode 260. The position of electrode 155 in FIG. 3B is termed herein a "centerline default position". If the cutting member 145 and electrode 155 were rotated so as to be close to an edge 262a or 262b of window 158 in outer sleeve 140, RF current could arc between the electrodes 155 and 260 and potentially cause a short circuit disabling the probe. Therefore, a robust and reliable stop mechanism is required which is described next.

As can be understood from FIGS. 1 and 2A-2B, the controller 165 can always determine in real time the rotational position of drive coupling 150 and therefore the angular or rotational position of the ceramic cutting member 145 and electrode 155 can be determined. A controller algorithm can further calculate the rotational angle of the electrode 155 away from the centerline default position as the Hall sensor 245 can sense lessening of magnetic field strength as a magnet 255a or 255b in the drive coupling 150 rotates the electrode 155 away from the centerline default position. Each magnet has a specified, known strength and the algorithm can use a look-up table with that lists fields strengths corresponding to degrees of rotation away from the default position. Thus, if the Hall signal responsive to the rotated position of magnet 255a or 255b drops a specified amount from a known peak value in the centerline default position, it means the electrode 155 has moved away from the center of the window 158. In one variation, if the electrode 155 moves a selected rotational angle away from the centerline position during RF energy delivery to the electrode, the algorithm turns off RF current instantly and alerts the physician by an aural and/or visual signal, such as an alert on the LCD screen 170 on handpiece 104 and/or on a screen on a controller console (not shown). The termination of RF current delivery thus prevents the potential of an electrical arc between electrode 155 and the outer sleeve electrode 260.

It can be understood that during use, when the electrode 155 is in the position shown in FIG. 3B, the physician may be moving the energized electrode over tissue to ablate or coagulate tissue. During such use, the cutting member 145 and electrode 155 can engage or catch on tissue which inadvertently rotate the electrode 155 out of the default centerline position. Therefore, the system provides a controller algorithm, herein called an "active electrode monitoring" algorithm, wherein the controller continuously monitors position signals generated by Hall sensor 245 during RF energy delivery in both an ablation mode and a coagulation mode to determine if the electrode 155 and inner sleeve 142 have been bumped off the centerline position. In a variation, the controller algorithms can be configured to then re-activate the motor drive 105 to move the inner sleeve 142 and electrode 155 back to the default centerline position if electrode 155 had been bumped off the centerline position. In another variation, the controller algorithms can be configured to again automatically deliver RF current to RF electrode 155 when it is moved back to the to the default centerline position. Alternatively, the controller 165 can require the physician to manually re-start the delivery of RF current to the RF electrode 155 when it is moved back to the to the centerline position. In an aspect of the invention, the drive coupling 150 and thus magnets 255a and 255b are attached to inner sleeve 142 and cutting member 145 in a pre-determined angular relationship relative to longitudinal axis 128 so that the Hall sensor generates signals responsive to magnets 255a, 255b is the same for all probes within a probe type to thus allow the controller algorithm to function properly.

Figure 8:
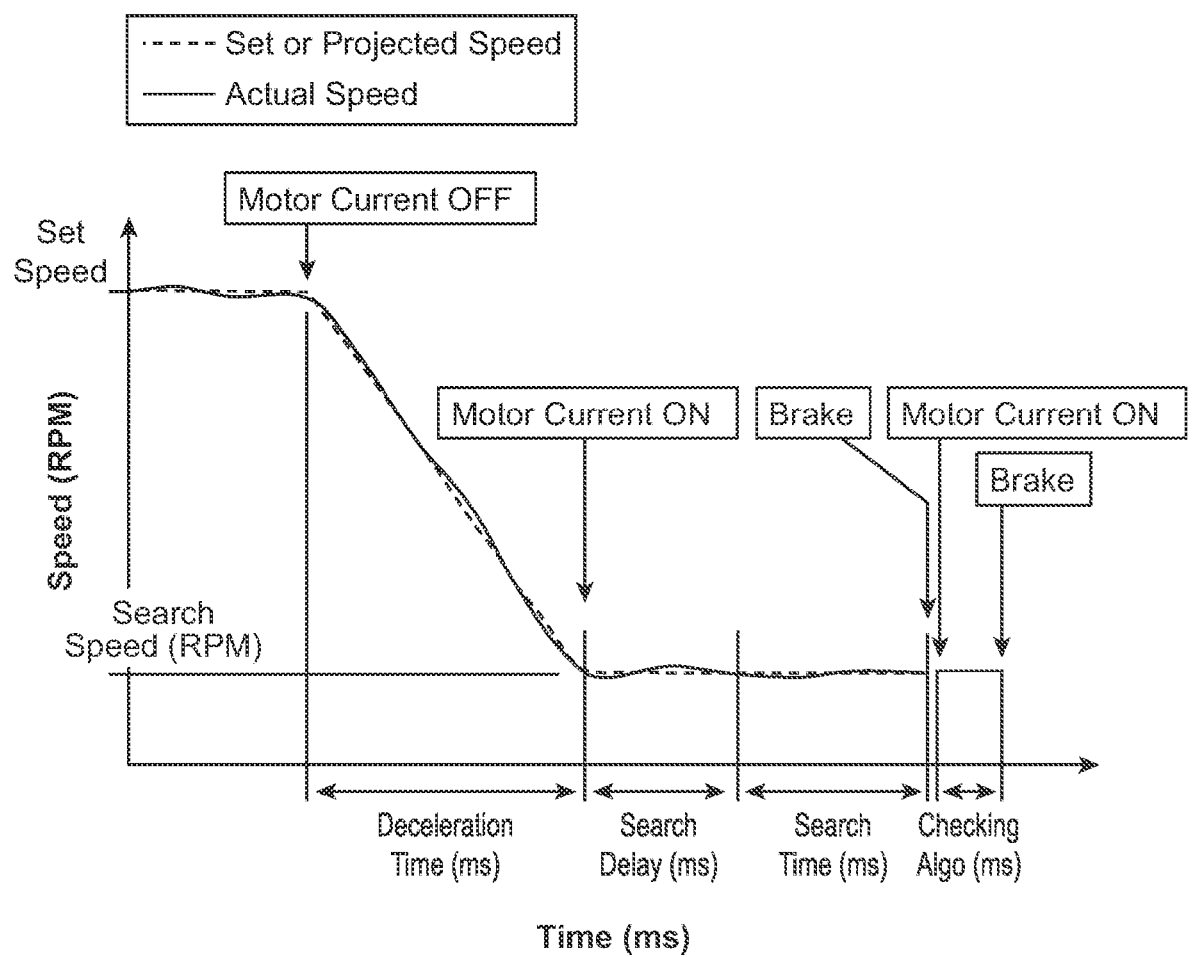
FIG. 8 is a chart relating to set speeds for a probe with a rotating cutting member as in FIGS. 1 and 3A that schematically shows the method used by a controller algorithm for stopping rotation of the cutting member in a selected default position.

Now turning to the stop mechanism or algorithms for stopping movement of a motor-driven component of working end 112, FIG. 8 schematically illustrates the algorithm and steps of the stop mechanism. In one variation, referring to FIG. 8, the stop mechanism corresponding to the invention uses (i) a dynamic braking method and algorithm to stop the rotation of the inner sleeve 142 and cutting member 145 (FIGS. 1, 3A-3B) in an initial position, and thereafter (ii) a secondary checking algorithm is used to check the initial stop position that was attained with the dynamic braking algorithm, and if necessary, the stop algorithm can re-activate the motor drive 105 to slightly reverse (or move forward) the rotation of drive coupling 150 and inner sleeve 142 as needed to position the cutting member 145 and electrode 155 within at the centerline position or within 0° to 5° of the targeted centerline default position. Dynamic braking is described further below. FIG. 8 schematically illustrates various aspects of controller algorithms for controlling the rotational speed of the cutting member and for stopping the cutting member 145 in the default centerline position.

In FIG. 8, it can be understood that the controller 165 is operating the probe 110 of FIGS. 1 and 3A-3B at a "set speed" which may be a PID controlled, continuous rotation mode in one direction or may be an oscillating mode where the motor drive 105 rotates the cutting member 145 in one direction and then reverses rotation as is known in the art. At higher rotational speeds such as 1,000 RPM to 20,000 RPM, it is not practical or feasible to acquire a signal from Hall sensor 245 that indicates the position of a magnet 255a or 255b in the drive coupling 150 to apply a stop algorithm. In FIG. 8, when the physician stop cutting with probe 110 by releasing actuation of an actuator button or foot pedal, current to the motor drive 105 is turned off. Thereafter, the controller algorithm uses the Hall sensor 245 to monitor deceleration of rotation of the drive coupling 150 and inner sleeve 142 until a slower RPM is reached. The deceleration period may be from 10 ms to 1 sec and typically is about 100 ms. When a suitable slower RPM is reached which is called a "search speed" herein (see FIG. 8), the controller 165 re-activates the motor drive 105 to rotate the drive coupling at a low speed ranging from 10 RPM to 1,000 RPM and in one variation is between 50 RPM and 250 RPM. An initial "search delay" period ranging from 50 ms to 500 ms is provided to allow the PID controller to stabilize the RPM at the selected search speed. Thereafter, the controller algorithm monitors the Hall position signal of magnet strength and when the magnet parameter reaches a predetermined threshold, for example, when the rotational position of drive coupling 150 and electrode 155 correspond to the centerline default position of FIG. 3B, the control algorithm then applies dynamic braking to instantly stop rotation of the motor drive shaft 151, drive coupling 150 and the motor-driven component of the probe. FIG. 8 further illustrates that the controller can check the magnet/drive coupling 150 position after the braking and stopping steps. If the Hall position signal indicates that the motor-driven component is out of the targeted default position, the motor drive 105 can be re-activated to move the motor-driven component and thereafter the brake can be applied again as described above.

Dynamic braking as shown schematically in FIG. 8 may typically stop the rotation of the drive coupling 150 with a variance of up to about 0°-15° of the targeted stop position, but this can vary even further when different types of tissue are being cut and impeding rotation of the cutting member 145, and also depending on whether the physician has completely disengaged the cutting member from the tissue interface when the motor drive is de-activated. Therefore, dynamic braking alone may not assure that the default or stop position is within a desired variance.

As background, the concept of dynamic braking is described in the following literature: https://www.ab.com/support/abdrives/documentation/techpapers/RegenOverview01.pdf and http://literature.rockwellautomation.com/idc/groups/literature/documents/wp/drives-wp004_-en-p.pdf. Basically, a dynamic braking system provides a chopper transistor on the DC bus of the AC PWM drive that feeds a power resistor that transforms the regenerative electrical energy into heat energy. The heat energy is dissipated into the local environment. This process is generally called dynamic braking with the chopper transistor and related control and components called the chopper module and the power resistor called the dynamic brake resistor. The entire assembly of chopper module with dynamic brake resistor is sometimes referred to as the dynamic brake module. The dynamic brake resistor allows any magnetic energy stored in the parasitic inductance of that circuit to be safely dissipated during the turn off of the chopper transistor.

The method is called dynamic braking because the amount of braking torque that can be applied is dynamically changing as the load decelerates. In other words, the braking energy is a function of the kinetic energy in the spinning mass and as it declines, so does the braking capacity. So the faster it is spinning or the more inertia it has, the harder you can apply the brakes to it, but as it slows, you run into the law of diminishing returns and at some point, there is no longer any braking power left.

In another aspect of the invention, a method has been developed to increase the accuracy of the stopping mechanism which is a component of the positioning algorithm described above. It has been found that each magnet in a single-use probe may vary slightly from its specified strength. As described above, the positioning algorithm uses the Hall effect sensor 245 to continuously monitor the field strength of magnets 255a and 255b as the drive coupling 150 rotates and the algorithm determines the rotational position of the magnets and drive coupling based on the field strength, with the field strength rising and falling as a magnet rotates past the Hall sensor. Thus, it is important for the algorithm to have a library of fields strengths that accurately correspond to degrees of rotation away from a peak Hall signal when a magnet is adjacent the sensor 245. For this reason, an initial step of the positioning algorithm includes a "learning" step that allow the controller to learn the actual field strength of the magnets 255a and 255b which may vary from the specified strength. After a new single-use probe 110 (FIG. 1) is coupled to the handpiece 104, and after actuation of the motor drive 105, the positioning algorithm will rotate the drive coupling at least 180° and more often at least 360° while the Hall sensor 245 quantifies the field strength of the particular probe's magnets 255a and 255b. The positioning algorithm then stores the maximum and minimum Hall signals (corresponding to North and South poles) and calibrates the library of field strengths that correspond to various degrees of rotation away from a Hall min-max signal position when a magnet is adjacent the Hall sensor.

In general, a method of use relating to the learning algorithm comprises providing a handpiece with a motor drive, a controller, and a probe with a proximal hub configured for detachable coupling to the handpiece, wherein the motor drive is configured to couple to a rotating drive coupling in the hub and wherein the drive coupling carries first and second magnets with North and South poles positioned differently relative to said axis, and coupling the hub to the handpiece, activating the motor drive to thereby rotate the drive coupling and magnets at least 180°, using a handpiece sensor to sense the strength of each magnet, and using the sensed strength of the magnets for calibration in a positioning algorithm that is responsive to the sensor sensing the varying strength of the magnets in the rotating drive coupling to thereby increase accuracy in calculating the rotational position of the drive coupling 150.

Another aspect of the invention relates to an enhanced method of use using a probe working end with an electrode, such as the working end 112 of FIGS. 1 and 3B. As described above, a positioning algorithm is used to stop rotation of the electrode 155 in the default centerline position of FIG. 3B. An additional "slight oscillation" algorithm is used to activate the motor drive 105 contemporaneous with RF current to the electrode 155, particularly an RF cutting waveform for tissues ablation. The slight oscillation thus provides for a form of oscillating RF ablation. The slight oscillation algorithm rotates the electrode 155 in one direction to a predetermined degree of rotation, which the controller algorithms determine from the Hall position signals. Then, the algorithm reverses direction of the motor drive to rotate in the opposite direction until Hall position signals indicate that the predetermined degree of rotation was achieved in the opposite direction away from the electrode's default centerline position. The predetermined degree of angular motion can be any suitable rotation that is suitable for dimensions of the outer sleeve window, and in one variation is from 1° to 30° in each direction away from the centerline default position. More often, the predetermined degree of angular motion is from 5° to 15° in each direction away from the centerline default. The slight oscillation algorithm can use any suitable PID controlled motor shaft speed, and in one variation the motor shaft speed is from 50 RPM to 5,000 RPM, and more often from 100 RPM to 1,000 RPM. Stated another way, the frequency of oscillation can be from 20 Hz to 2,000 Hz and typically between 40 Hz and 400 Hz.

While the above description of the slight oscillation algorithm is provided with reference to electrode 155 on a rotating cutting member 145 of FIG. 3B, it should be appreciated that a reciprocating electrode 212 as shown in the working end 200C of FIG. 6 end could also be actuated with slight oscillation. In other words, the hook shape electrode 212 of FIG. 6 could be provided with a frequency of oscillation ranging from 20 Hz to 2,000 Hz and typically between 40 Hz and 400 Hz.

Figure 9A:
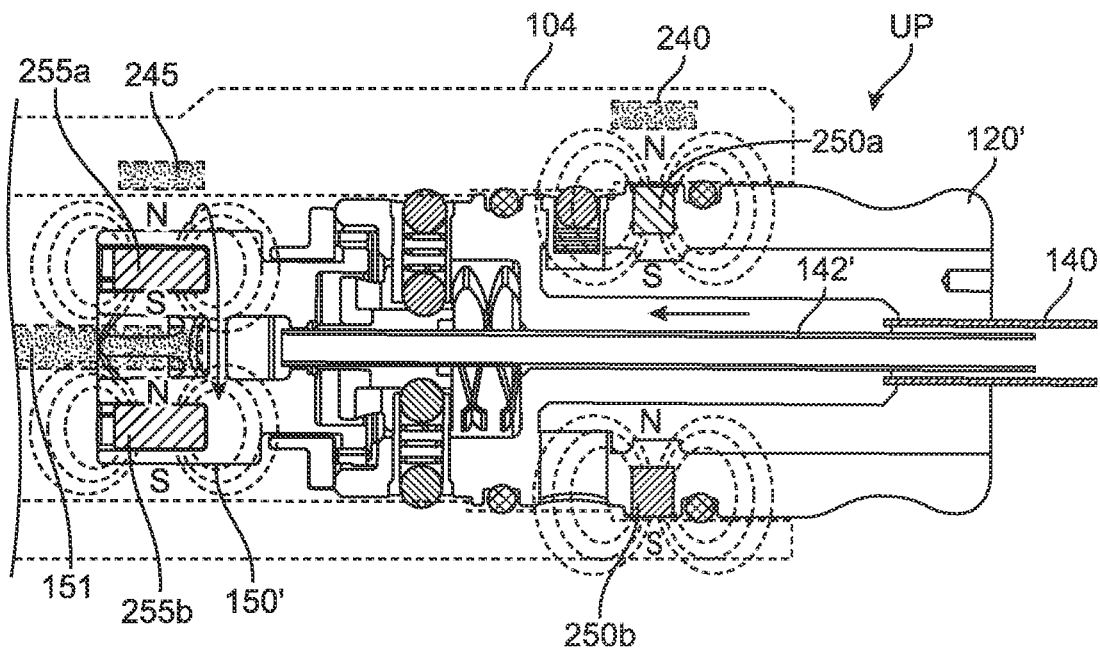
FIG. 9A is a longitudinal sectional view of a probe hub that is similar to that of FIG. 2A, except the hub of FIG. 9A has an internal cam mechanism for converting rotational motion to linear motion to axially reciprocate an electrode as in the working end of FIG. 5, wherein FIG. 9A illustrated the magnets in the hub and drive coupling are the same as in FIG. 2A and the hub is in an upward facing position relative to the handpiece.
Figure 9B:
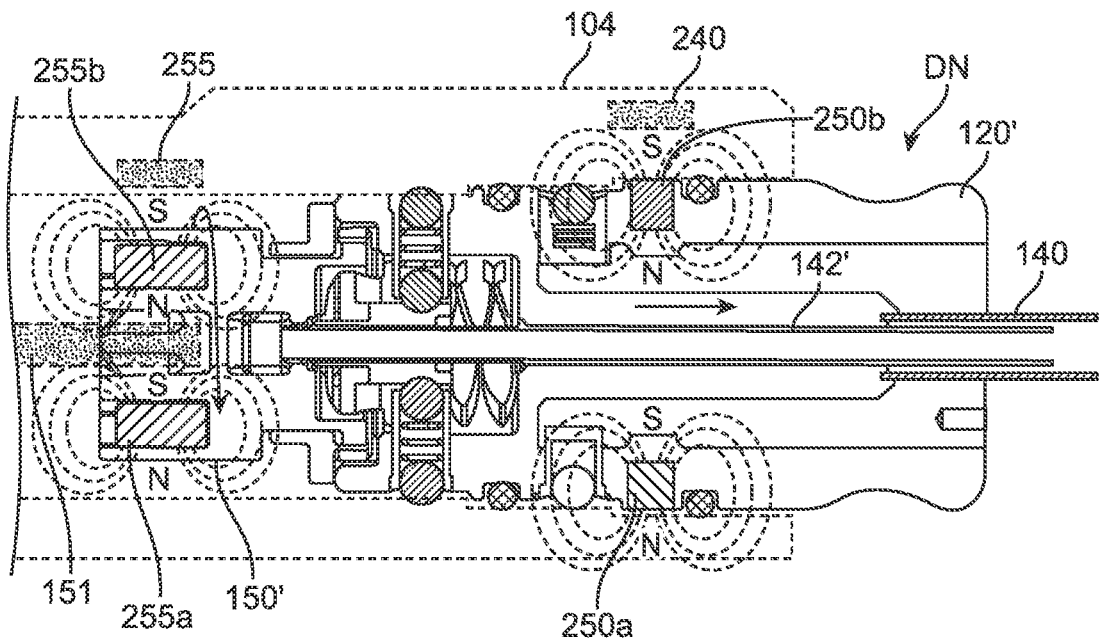
FIG. 9B is a sectional view of the hub of FIG. 9A rotated 180° in a downward facing position relative to the handpiece.

FIGS. 9A-9B are longitudinal sectional views of a probe hub 120' that corresponds to the working end 200B of FIG. 5 which has a reciprocating electrode 210. In FIGS. 9A-9B, the handpiece 104 and Hall affect sensors 240 and 245 are of course the same as described above as there is no change in the handpiece 104 for different types of probes. The probe hub 120' of FIGS. 9A-9B is very similar to the hub 120 of FIGS. 2A-2B with the first and second identification/orientation magnets 250a and 250b being the same. The third and fourth rotation al position magnets 255a and 255b also are the same and are carried by drive coupling 150'. The probe hub 120' of FIGS. 9A-9B only differs in that the drive coupling 150 rotates with a cam mechanism operatively coupled to inner sleeve 142' to convert rotational motion to linear motion to reciprocate the electrode 210 in working end 200B of FIG. 5. A similar hub for converting rotational motion to linear motion is provided for the working ends 200C and 200D of FIGS. 6 and 7, respectively, which each have a reciprocating component (212, 218) in its working end.

Backpressure Detection Algorithm

Figure 10:
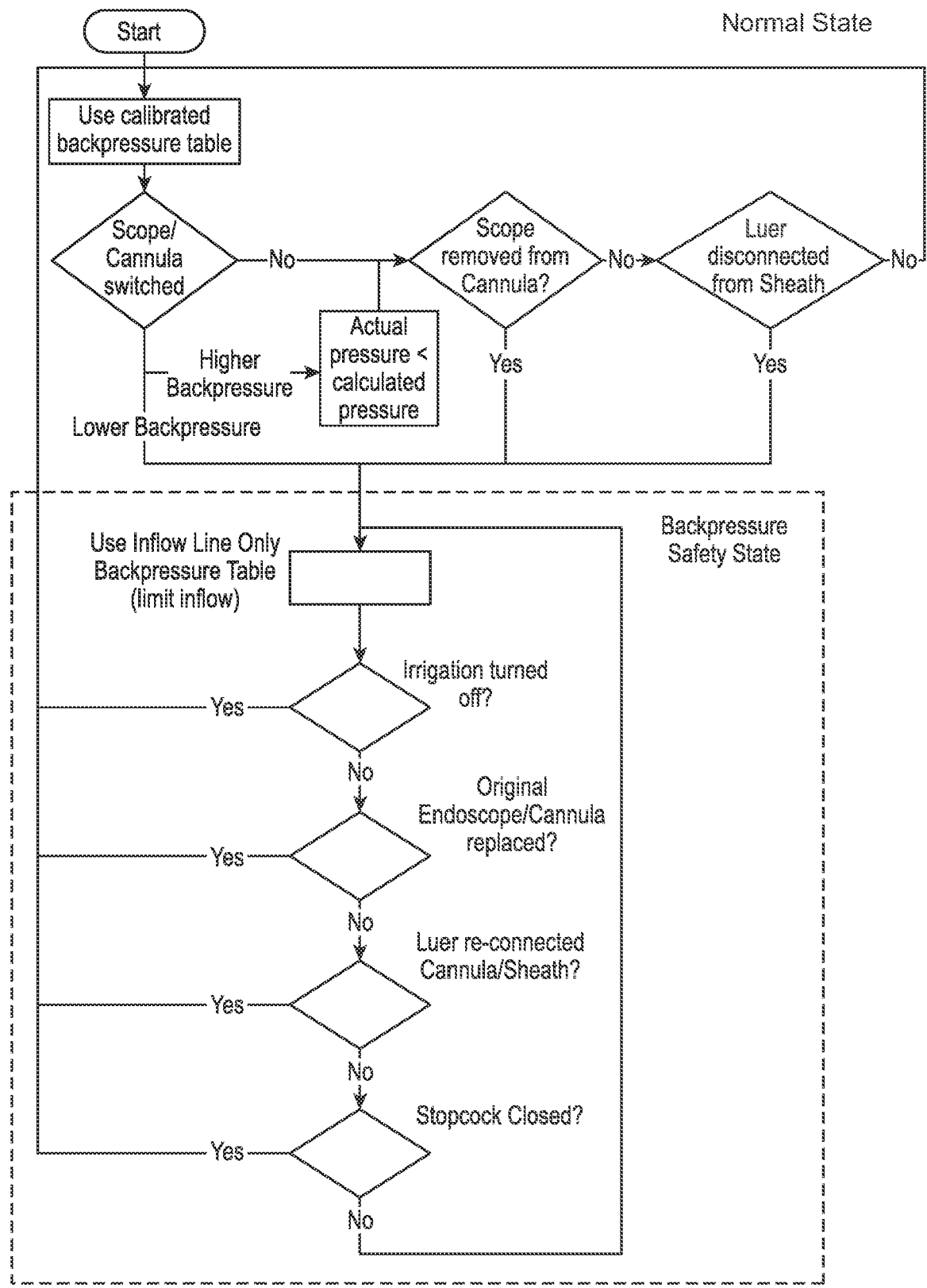
FIG. 10 is a diagram illustrates subsystems for use in a pressure control feedback loop in a controller and backpressure conditions for entering and exiting a mode of operation in a safety state when a significant change in backpressure is detected.
Figure 11:
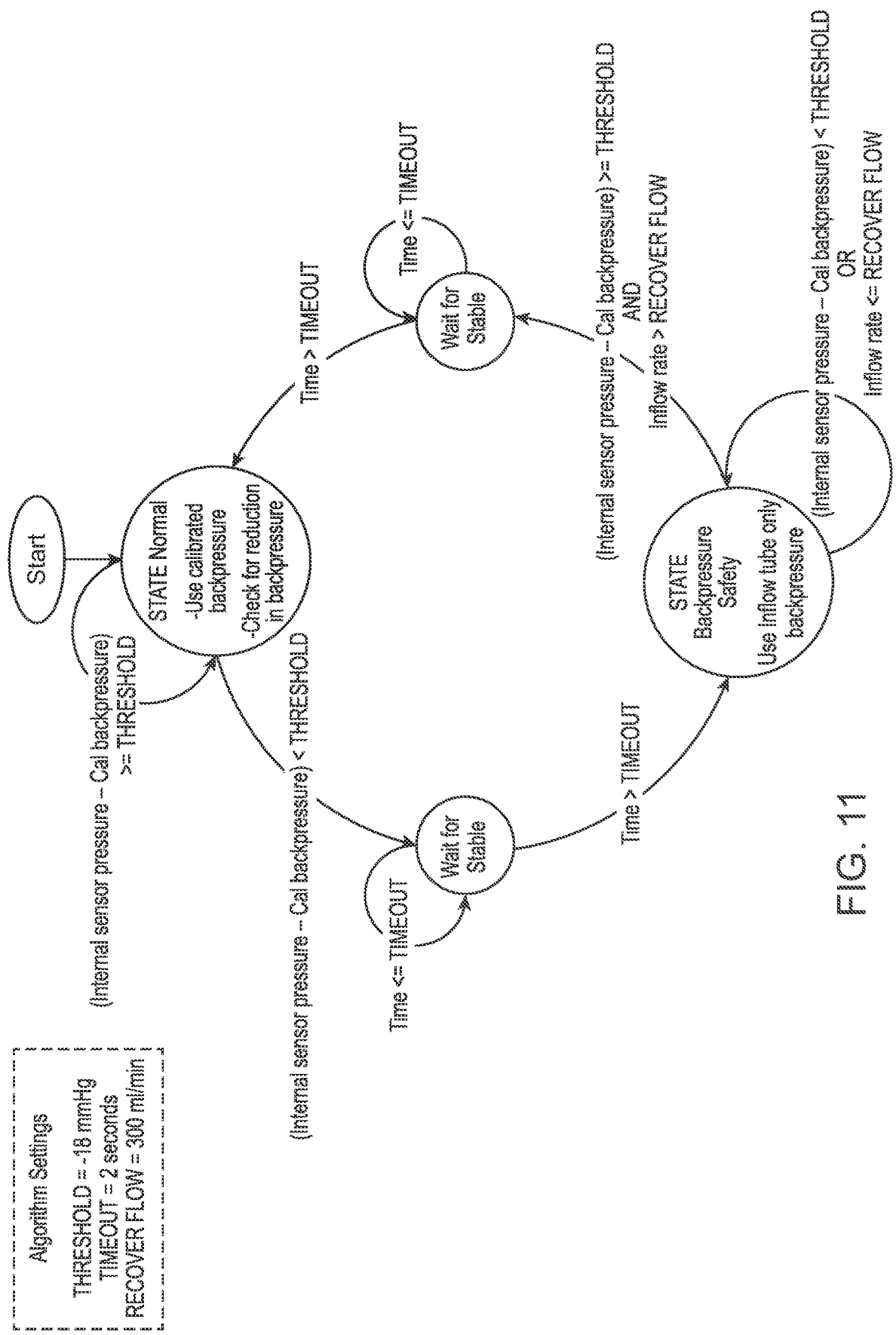
FIG. 11 is a diagram illustrating the software algorithm for entering and exiting the safety state referred to in FIG. 10.
Figure 12:
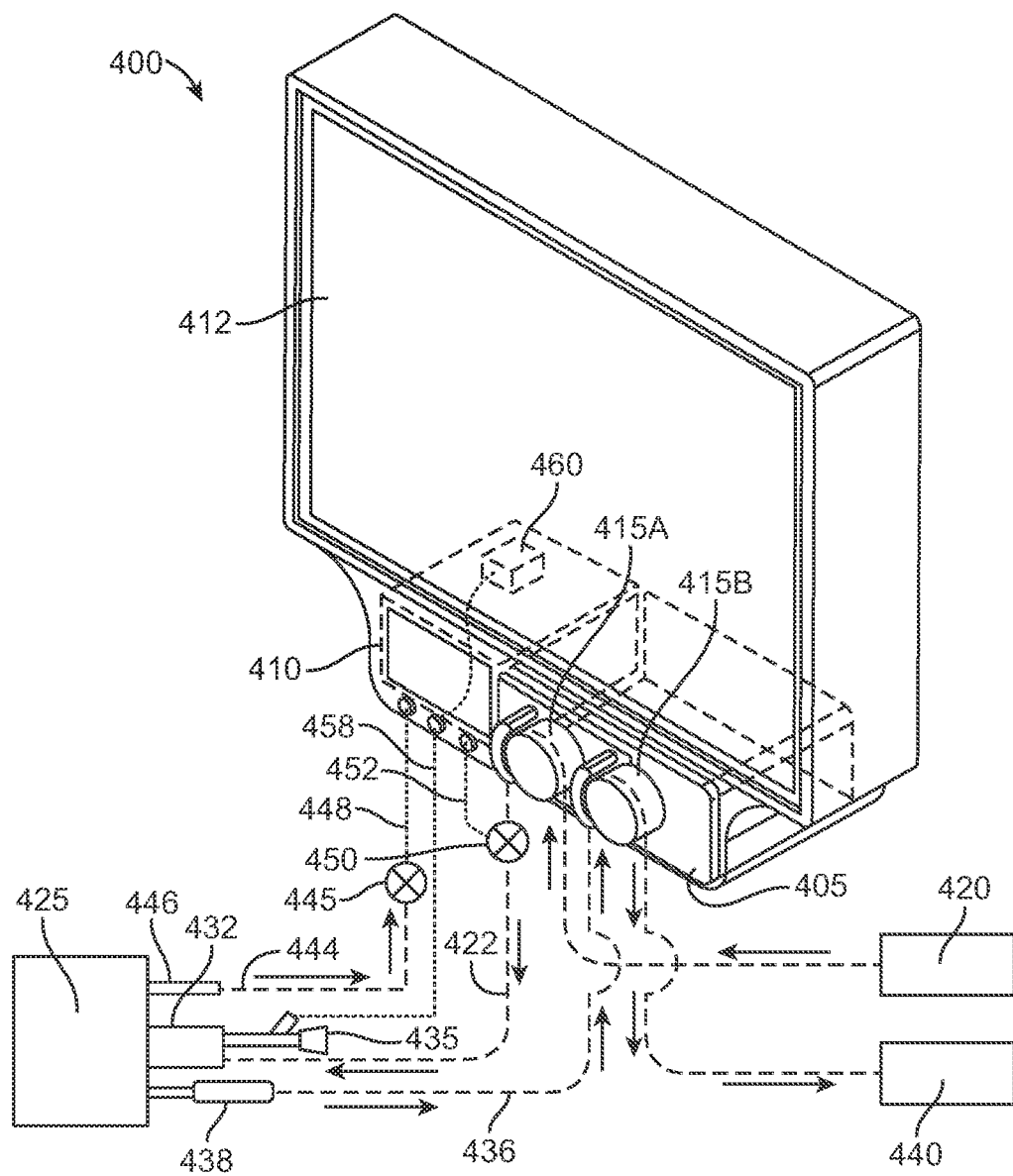
FIG. 12 illustrates an integrated videoscopic system which comprises a base unit that houses a dual pump fluid management system, a controller for controlling the fluid management system and an electrical source for powering an arthroscopic or similar cutting device, in RF source for energizing and electrode arrangement in a cutting device, a video monitor for displaying images provided by the endoscope, and an image processing system for processing images signals from an imaging sensor carried by the endoscope.

Now turning to FIGS. 10-12, a controller and controller algorithms are described that are configured to control pressure in the working space using two different subsystems and methods. In a first system and method of pressure sensing, a pressure sensor outside the patient's body communicates with a dedicated static fluid channel extending into the working space which provides for highly accurate readings of actual pressure in the working space. In a second method of pressure sensing, a flow line pressure sensor is provided in an inflow line that is active and carries distention fluid into the working space.

FIG. 12 is a schematic illustration of a surgical system 400 that integrates the fluid management system 405, controller 410 and a video monitor 412 into a single unit. The system 400 can further include an electrical source (not shown) for providing power to a motor drive of an arthroscopic shaver and an RF source (not shown) for energizing an electrode arrangement carried by such an arthroscopic shaver. In FIG. 12, the fluid management system 405 includes an inflow pump 415A and outflow pump 415B. The pumps can be peristaltic pumps as are known in the art. A fluid source 420 comprising a saline bag can be coupled to the inflow line 422 to carry distention fluid to the working space 425, which for example can be a patient's knee, shoulder, hip or other joint. Typically, the inflow line 422 is connected to a cannula 432 that accesses the working space and receives an endoscope 435 which is introduced through the cannula. An outflow line 436 is coupled to an instrument 438, such as a shaver, that is introduced into the working space 425 shown in FIG. 12. The outflow line 436 is coupled to the outflow pump 415B to carry fluid outwardly from the working space 425 to a collection reservoir 440. Thus, it can be understood that the controller 410 is configured to control the inflow pump 415A and the outflow pump 415B using a pressure feedback loop or algorithm to maintain a set pressure in the working space 425 as is known in the art.

As described above, the first system pressure sensing system uses the static fluid channel 444 coupled to a first pressure sensor 445 as shown FIG. 12, wherein such a static channel communicating through cannula 446 with the working space 425 can be relatively short in length. Thus, there will be negligible pressure losses in such a static channel 444 and the sensed pressure will be very accurate. This in turn allows for very fast response times in the controller's pressure control loop. The pressure sensor 445 sends pressure signals to the controller by cable 448. However, it may not always be possible to use the first sensor 445 and method for the direct sensing of pressure to send signals to the pressure control loop.

In the system variation shown in FIG. 12, the second system for providing signals to the pressure control loop uses a second pressure sensor 450 that is coupled to the inflow line 422 and measures pressure of the fluid flow therein. The pressure sensor 450 may be in a cassette (not shown) that carries the inflow line and sends signals to the controller 410 through cable 452.

Still referring to FIG. 12, in one system variation, the controller 410 is capable of measuring pressure in the working space through both the first and second methods described above, and the controller 410 can automatically switch from the first system using sensor 445 to the second system using sensor 450 when the first system is determined to be inaccurate.

In another variation, the system can be configured to use the second system and method that utilizes the flow line pressure sensor 450 and a controller algorithm that calculates pressure in the working space 425. In this variation, since the flow line pressure sensor 450 is upstream of the cannula 422 and endoscope 435 and a portion of the inflow line 422, there will be several pressure losses that need to be measured and taken into account by the controller algorithm to then calculate the pressure in the working space 425. The pressure losses include the head pressure and the backpressure due to the restricted flow through the cannula, endoscope and the inflow line 422. To account for these pressure losses, the controller 410 is configured to prompt the physician before the start of any surgical procedure to perform a "backpressure calibration" of the system and components being used before the instruments are introduced into the working space. The backpressure calibration step uses a calibration algorithm to then operate the inflow pump 415A to provide a plurality of fluid inflow rates ranging from the maximum flow rate to the minimum flow rate and thereafter records the backpressure in a backpressure or BP table for each of the flow rates. Thereafter, during use of the system in a surgical procedure, the controller algorithm receives signals from the flow line sensor 450 and subtracts the pre-recorded backpressure readings at any given flow rate from the sensed pressure to calculate the pressure in the working space 425.

It can be easily understood that the calibrated backpressure readings are critical for safe operation of the fluid management system 405, wherein the controller software includes a pressure control loop that operates the inflow and outflow pumps to maintain a set pressure in the working space. It can be further understood that if the physician decides to exchange instruments, such as the endoscope or cannula in the middle of a surgical procedure, the backpressure caused by the new instruments will likely differ from that of the original instruments due to different flow channel diameters or lengths of the exchanged instruments. Thus, it can be understood that if the backpressure changes during due to instrument exchange, then the calculated pressure would be inaccurate and could cause the fluid management system to over-pressurize the joint without the physician knowing about the over-pressure condition which could be a hazard to the patient's health.

The exchange of instruments could cause the backpressure to increase or decrease. In one case, if the endoscope and cannula were exchanged and caused the backpressure to be higher than originally calibrated, the controller's pressure control loop would calculate the pressure to be higher than actual working space pressure during a procedure and the joint would be under-pressurized. In the opposite case, if the endoscope and cannula were exchanged resulting in the backpressure to be lower than originally calibrated, then the controller's pressure control loop would calculate the pressure to be lower than the actual pressure and the working space would be over-pressurized by the fluid management system. The amount of over-pressurization would be equal to the difference in backpressure between the original endoscope/cannula combination and the replacement endoscope and cannula for any given flow rate. It should be noted that at a "no flow" condition, the calculated pressure will be accurate. The safety concern arises when there is an actual fluid flow through the inflow channel 422. In this situation, there could be significant degree of over-pressurization which could be a hazard to the patient over the duration of a procedure.

There are also other conditions of lesser importance in which backpressure could be reduced during a procedure thus causing an inaccurate calculated pressure. In one case, the physician may remove the endoscope from the cannula immediately after introducing the cannula into the working space to allow fluid to drain outwardly from the working space to clear any debris or blood to thereby provide better visibility. In another case, the Luer coupling of the inflow tubing 422 may become disconnected from the cannula 432 and the calculated pressure would not be accurate. In these two circumstances, it would be useful to lower the fluid inflow rate to prevent fluid from spurting out of the working space or out of the disconnected inflow tubing. Both of these situations would unnecessarily waste the distention fluid.

In order to address the above-described problems, and most importantly for detecting an instrument exchange, a controller detection algorithm is provided which operates continuously in the background of the pressure control loop to determine if the calculated pressure ever goes negative or below a predetermined threshold level. In one variation, the threshold level is a preset ranging between 5 mm Hg and 25 mm Hg, for example 18 mm Hg. If the backpressure drops below the threshold level, this would indicate that the backpressure was lowered in some way, since the calculated pressure is defined as:

Calculated Pressure=Sensor Pressure−Calibrated Backpressure(inflow rate)

Thus, the detection algorithm observes the calculated pressure for a defined detection interval, for example between 1 to 10 seconds or more often between 2 to 5 seconds, to determine that there is been an instrument exchange or other malfunction. The time interval is required so that brief oscillations of pressure which might occur under normal conditions would not cause the detection algorithm to trigger falsely. If the endoscope and/or cannula were in fact exchanged, the condition would exist continuously over the detection interval and in fact continue indefinitely. Once the condition is detected, the detection algorithm is adapted to immediately stop using the calibrated backpressure table since the characteristics of the replacement endoscope and/or cannula are unknown. Thereafter, the algorithm will operate the system in a "safety state" by reverting to the minimum backpressure known to the system, which consists of the backpressure of the inflow tubing alone.

In this case, calculated pressure becomes:

Calculated Pressure=Sensor Pressure−Inflow Line Backpressure(inflow rate)

where:

For Inflow rate=0 ml/min: Real Pressure=Calculated Pressure

For Inflow rate>0 ml/min: Real Pressure<Calculated Pressure

FIG. 10 is a diagram illustrating the conditions for entering and exiting the above described safety state. FIG. 11 is a diagram illustrating the software algorithm for entering and exiting the safety state. Thus, the detection algorithm creates the safest possible condition which bases the calculated pressure on the least amount of backpressure that could ever be present in the fluid management system. Therefore, the calculated pressure will always be higher than the actual pressure in the working space, preventing any hazardous over-pressure condition.

Another advantage of using the detection algorithm is that in the reduced backpressure mode of operation, the rate of fluid flow provided by the inflow pump will be lowered to a low recovery rate (e.g., between 100 ml/min and 300 ml/min) because the calculated pressure will be higher than actual pressure in the working space, and the error in the PID control loop will be reduced thus causing the control loop to immediately reduce the inflow rate since the system determines the working space is at the set pressure before the set pressure is actually achieved.

This aspect of the detection algorithm also means that when the endoscope is removed from the cannula, as in the commonly done at the start of a procedure, the fluid inflow will be reduced in that instance which will greatly reduce the occurrence of a spurt or geyser of fluid exiting the cannula. Thus, the detection algorithm can reduce the amount of distention fluid wasted before the endoscope is re-inserted into the cannula. Also, if the Luer connection to the inflow tubing was disconnected from the cannula during a procedure as described above, then the algorithm will reduce the fluid inflow rate and the amount of fluid loss outside the patient will be greatly reduced.

In another aspect of the invention, it is also important to note that the detection algorithm will exit the safety condition automatically whenever the sensed hazard is eliminated such that no physician intervention is required. That is, if the correct or original endoscope and cannula were to be re-introduced into the procedure the controller and detection algorithm would be working again automatically. In order to accomplish such an automatic exit from the sensed hazard, the detection algorithm is adapted to constantly monitor the real calculated pressure in the background (using the calibrated backpressure table) to determine if the pressure becomes positive again (that is, greater than the entering state threshold). It can be appreciated that this condition can only be confirmed when under significant fluid inflows in the system. At "no flow" or low fluid flow, the calculated pressure will appear to be normal. Therefore, the detection algorithm is adapted to not exit the safety state until there is an adequate predetermined flow rate to then determine that the correct or original endoscope and cannula are again in use. This recovery condition must also be constant over a detection interval which can be the same amount of time that is required to enter the safety state to ensure the state is not prematurely exited.

The safety state is also automatically exited if a stopcock on the inflow tubing is closed, because this causes a sudden increase in pressure sensed by the pressure sensor, with minimal to no backpressure, since the endoscope and cannula have been suddenly cut-off. This again is advantageous since the physician will likely close the stopcock before exchanging the endoscope and cannula. Therefore, at the time the physician attaches the correct or original instruments again, the inflow pump will already be back in the normal operating state.

Figure 13:
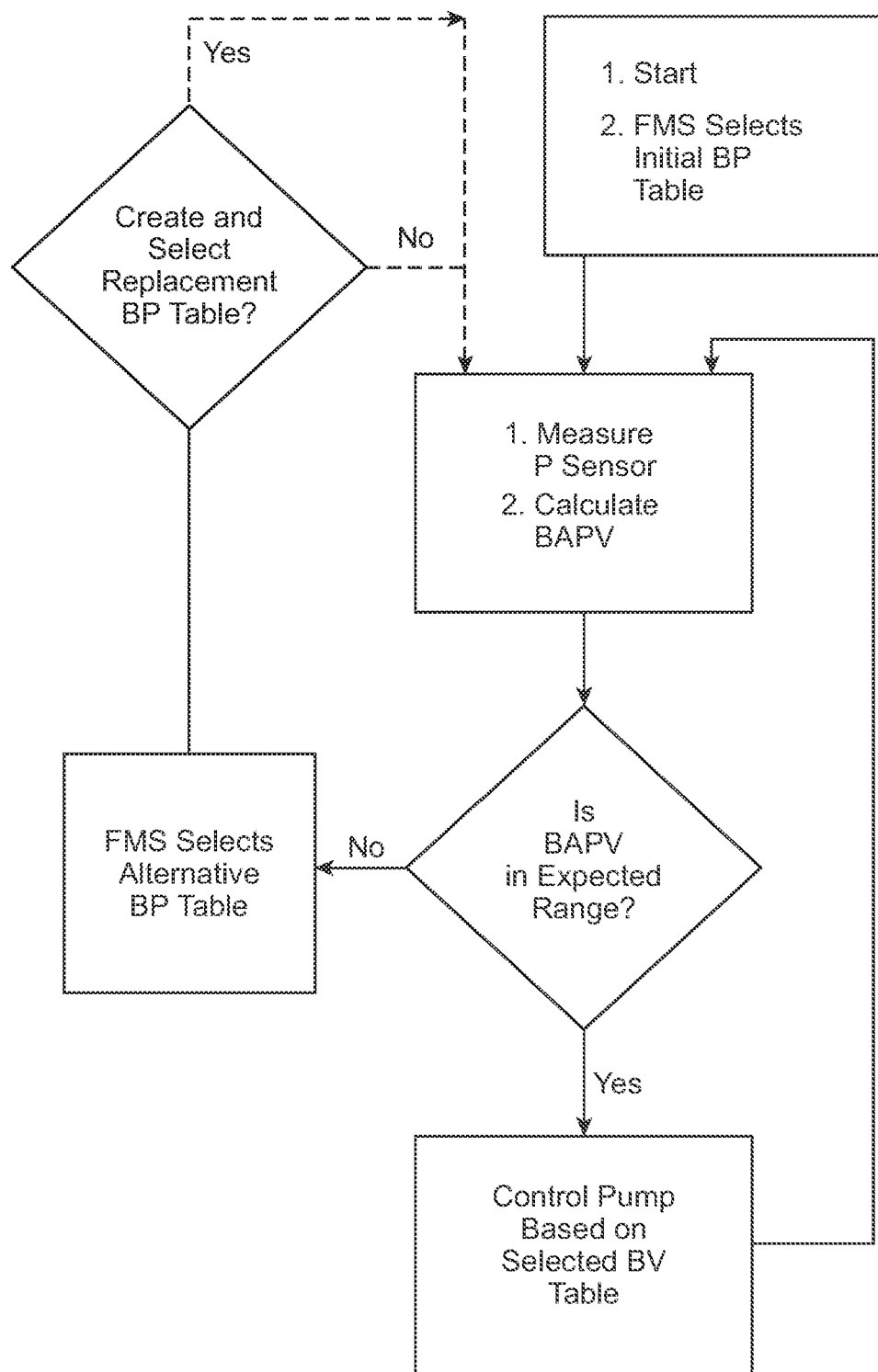
FIG. 13 is a logic diagram illustrating an alternative pressure adjustment protocol in accordance with the principles of the present invention.

Referring now to FIG. 13, a diagram of the operation of the fluid management system (FMS) of FIG. 12 is shown which performs the pressure management functions described above. More specifically, the FMS may be used to adjust pressure values measured by pressure sensor 450 to accurately represent an actual pressure present in the working space 425 in real time. In exemplary methods, and initial backpressure or BP table is loaded into the controller 410. For example, pressure sensor 450 maybe used to measure the combined backpressures of the inflow line 422 and cannula 432 by pumping fluid using inflow pump 415A while the outlet end of the cannula is in free space, typically emptying the fluid 405 from the inflow pump into a bucket or other open receptacle. The BP table is generated by storing the backpressure values at a plurality of different pump flow rates or pump speeds (the inflow pump for 415A is typically a positive displacement peristaltic pump where the pump speed is directly representative of the pump flow rate). By assembling the cannula together with the arthroscope or other endoscope to be used in the procedure, as well as any other flow components which may be part of the procedure, the initial backpressure table will provide a very accurate listing of the backflow pressures at different flow rates.

After the initial backpressure table has been generated, typically at the very outset of the procedure, the assembly of the cannula, arthroscope, and any other system components may then be introduced to the body cavity or other surgical worksite in a conventional manner and the surgical protocol initiated. As part of the procedure, the inflow pump 415A will be actuated to deliver fluid 405 to the working space while the pressure within the working space is monitored using the pressure sensor 450. The controller 410 will be programmed to control the speed of inflow pump (optionally, that of outflow pump 415B as well) to maintain a pressure within the working space at a desired set point. The control algorithm may be any conventional algorithm, such as proportional, interval, durative, or a combination thereof, such as PID control. The control algorithm then will try to maintain the pressure within the working space 425 at a value equal to the set point. This will be done by calculating or adjusting a the fluid inflow or outflow rates to the working space and the calculated pressure is derived from the measured pressure value from pressure sensor 450. In particular, a backpressure derived from the initial backpressure table is subtracted from the pressure measured by the pressure sensor 450 based on the flow rate of fluid through the inflow line 422 and cannula 432 to the work space.

Pressure control using the initial backpressure table will be sufficient so long as the system configuration is not changed so that the backpressure between the sensor and the working space does not change in a significant way. Such changes may occur, for example, if the cannula is changed out during the procedure period, and in such instances the system will continuously monitor the adjusted pressure value, also referred to as the backpressure-adjusted pressure value (BAPV), to assure that it has not fallen outside of an expected adjusted pressure range.

As shown in FIG. 13, the software of the controller 410 will continuously check to see if the BAPV is within the expected range. So long as it stays within the range, the pump will be controlled using the initial backpressure table. Should the controller 410 detect that the BAPV is outside of the expected range, however, the FMS will then switch to using an alternative backpressure table which is typically programmed into the controller. The alternative backpressure table represents backpressure values characteristic of the inflow line 422 only. As described above, such backpressure values will not necessarily be accurate, but will be conservative since they drive the system to deliver less fluid and maintain a lower pressure within the surgical site than would be optimum. If the alternative backpressure table were not used, there would be a risk that the system would deliver excess fluid to the workspace and risk over-pressuring the workspace which could be deleterious to the patient.

Referring still to FIG. 13, after the FMS has gone into the alternative mode where pressure control is based on the alternative backpressure table, a further system adjustment may optionally be made. The physician may at any time after the BAPV has fallen outside of the expected initial range, choose to create a replacement BP table. The replacement BP table generated in a manner analogous to generation of the initial BP table, but using a cannula, endoscope, and other system configuration as has been adjusted during the procedure which was the cause of the deviation outside of the initial BAPV range. Once such a replacement BP table has been generated, the system can use the replacement BP table until the BAPV falls outside of the replacement range.

Also, a further FMS option is to allow the system to return to using the initial backpressure table if the initial BAPV returns to a value within the initial BAPV range. Typically, this option would be available only if a replacement BP table has not been put into place.

In another aspect of the invention, referring to the videoscopic system of FIG. 12, it can be understood that the endoscope 435 in one variation has a distal electronic image sensor that is coupled by cable 458 to a video imaging processor 460 in the controller 410 for processing the image for display. In one system variation, the video processor is adapted to observe the video image signals and provide a control signal to the controller in response to observation of at least one environmental condition in the video image or video image signals. Upon observation of a particular environmental condition, then the controller can signal the physician within oral visual signal or adjust a parameter of the medical system, which can include the operation of the resecting or ablation device.

In general, a medical system of the invention comprises a videoscopic system including an endoscope coupled to an image display adapted to display video images of a working space, a fluid management system configured to provide fluid flows through the working space, and a video processor adapted to observe the video image signals and provide a control signal to a controller in response to observation of at least one environmental condition in said video images or signals.

The environmental condition of interest can be at least one of the following: color, light intensity, color intensity, contrast, focus, blurring, fluid bubbling, collapse of the working space, or a surgical or diagnostic tool in the field of view.

In one example, color in the video image or signals can indicate blood in the fluid-filled working space and the controller responsive to the control signal can adjust or increase the rate of fluid flow through the working space to clear the blood and improve endoscopic vision. In another variation, the color may indicate bone debris in the fluid-filled working space and the controller responsive to the control signal increases the rate of fluid flow through the working space. In another variation, the color can indicate blood in the fluid-filled working space and the controller responsive to the control signal can increase fluid pressure in the working space to tamponade the bleeding site.

In another variation, the imaging processor 460 can detect that light intensity is above or below a selected light intensity level and the controller responsive to the control signal can adjust light intensity to improve endoscopic vision.

In another variation, the imaging processor can include a thermal IR sensor to detect fluid temperature and the controller responsive to the control signal relating to fluid temperature adjusts the rate of fluid flow through the working space. In another variation, In another variation, the imaging processor can be configured to detect fluid bubbling and the controller responsive to the control signal can change the rate of fluid flow through the working space.

In another variation, the imaging processor can observe absence of a treatment tool in the field of view and the controller responsive to the control signal it can disable activation of any tool in the working space, such as a endoscopic shaver with the motor driven cutter or an RF ablation device.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A system for treating tissue, comprising:
   a fluid management system including a pump connectable to a fluid source;
   an inflow line configured to removably connect to a cannula for delivering a fluid flow from the pump into a working space;
   a flow pressure sensor located to measure flow pressure in the inflow line and produce a measured pressure value; and
   a controller connected to the pump and the flow pressure sensor, wherein the controller is configured (1) to maintain a pressure set point by controlling a pump speed based on an initial backpressure-adjusted pressure value (BAPV) calculated by subtracting a backpressure value selected from an initial backpressure table from the measured pressure value and (2) to monitor the initial BAPV to determine if the initial BAPV remains within an expected initial BAPV range, wherein the initial backpressure table provides backpressure values measured while operating the fluid management system at different pump speeds when the pump is connected to the inflow line and the cannula, and the distal end of the cannula is in a first free space, the first free space comprising a first receptacle.

2. The system of claim 1, wherein the controller is further configured to continue maintaining the pressure set point by controlling the pump speed based on the initial BAPV for so long as the initial BAPV remains within the expected initial BAPV range.

3. The system of claim 1, wherein the controller is further configured to access an alternative backpressure pressure table representing backpressure values between the flow pressure sensor and an end of the inflow line in a second free space at different flows generated by the pump when the initial BAPV falls outside of the expected initial BAPV range, the second free space comprising a second receptacle.

4. The system of claim 3, wherein the end of the inflow line is configured to removably connect to a cannula adapted to deliver fluid flow from the inflow line to the working space in the body.

5. The system of claim 3, wherein the controller is further configured to control the pump speed based on an alternative BAPV calculated by subtracting a value selected from the alternative backpressure table based on pump speed from the measured pressure value and when the monitored initial BAPV falls outside of the expected initial BAPV range.

6. The system of claim 5, wherein the controller is further configured to re-access the initial backpressure pressure table when the initial BAPV returns to a value within the initial BAPV range.

7. The system of claim 1, wherein the controller is further configured to access a replacement backpressure table generated by measuring backpressures at multiple flow rates produced by the pump when connected to the inflow line and a replacement cannula after the monitored initial BAPV falls outside of the expected initial BAPV range.

8. The system of claim 1, wherein the pump comprises an inflow unit connected to the inflow line and an outflow unit connected to an outflow line.

9. The system of claim 8, further comprising an endoscope configured for minimally invasive insertion into the working space, said endoscope further configured for removable attachment to the inflow line and having a lumen for delivery of the fluid from the fluid source.

10. The system of claim 9, further comprising an interventional tool configured for insertion through the lumen of the endoscope and having an extraction channel for connection to the outflow line.

11. A method for treating tissue, comprising:
(a) pumping fluid through an inlet line connected to a cannula having a distal end in a surgical site using a pump;
(b) measuring a pressure value using a pressure sensor in the inlet line;
(c) calculating an initial backpressure-adjusted pressure value (BAPV) by subtracting a backpressure value selected from an initial backpressure table from the measured pressure value, wherein the initial backpressure table provides backpressure values measured while pumping fluid at different pump speeds while the pump is connected to the inflow line and the cannula and while the distal end of the cannula is in a first free space, the first free space comprising a first receptacle;
(d) controlling a pump speed of the pump to maintain the initial BAPV at a pressure set point;
(e) monitoring the initial BAPV to determine if the initial BAPV remains within an expected initial BAPV range; and
(f) controlling the pump speed to maintain the initial BAPV at the pressure set point at for so long as the initial BAPV remains within the expected initial BAPV range.

12. The method of claim 11, further comprising accessing an alternative backpressure pressure table including backpressure values between the flow pressure sensor and an end of the inflow line in a second free space at different flows generated by the pump when the monitored value of the initial BAPV falls outside of the expected initial BAPV range, the second free space comprising a second receptacle.

13. The method of claim 12, further comprising:
(g) calculating an alternative backpressure-adjusted pressure value (BAPV) by adding a backpressure value selected from the alternative backpressure table to the measured pressure value; and
(h) controlling pump speed to maintain the alternative BAPV at the pressure set point.

14. The method of claim 13, further comprising:
(k) monitoring the initial BAPV to determine if the initial BAPV has returned to a value within the expected initial BAPV range; and
(l) controlling pump speed to maintain the initial BAPV at the pressure set point when the initial BAPV returns to a value within the initial BAPV range.

15. The method of claim 11, further comprising accessing a replacement backpressure table generated by measuring backpressures at multiple flow rates produced by the pump when connected to the inflow line and a replacement cannula after the initial BAPV falls outside of the initial BAIN range.

16. The method of claim 15, further comprising:
(g) calculating a replacement BAPV by adding a backpressure value selected from the replacement backpressure table to the measured pressure value; and
(h) controlling pump speed to maintain the replacement BAPV and the pressure set point.

17. The method of claim 11, wherein the surgical site is a joint cavity.

* * * * *